US010705087B2

(12) United States Patent
Takeuchi et al.

(10) Patent No.: US 10,705,087 B2
(45) Date of Patent: Jul. 7, 2020

(54) DETECTION METHOD FOR NTRK3 FUSION

(71) Applicant: JAPANESE FOUNDATION FOR CANCER RESEARCH, Tokyo (JP)

(72) Inventors: Kengo Takeuchi, Tokyo (JP); Yuki Togashi, Tokyo (JP); Seiji Sakata, Tokyo (JP); Satoko Baba, Tokyo (JP)

(73) Assignee: JAPANESE FOUNDATION FOR CANCER RESEARCH, Tokoyo (JP)

( * ) Notice: Subject to any disclaimer, the term of this patent is extended or adjusted under 35 U.S.C. 154(b) by 612 days.

(21) Appl. No.: 14/907,689

(22) PCT Filed: Jul. 25, 2014

(86) PCT No.: PCT/JP2014/069737
§ 371 (c)(1),
(2) Date: Jun. 30, 2016

(87) PCT Pub. No.: WO2015/012397
PCT Pub. Date: Jan. 29, 2015

(65) Prior Publication Data
US 2016/0305943 A1 Oct. 20, 2016

(30) Foreign Application Priority Data
Jul. 26, 2013 (JP) ................................ 2013-155711

(51) Int. Cl.
| C12Q 1/68 | (2018.01) |
| G01N 33/574 | (2006.01) |
| C12Q 1/6886 | (2018.01) |
| G01N 33/50 | (2006.01) |
| A61K 31/277 | (2006.01) |
| A61K 31/553 | (2006.01) |

(52) U.S. Cl.
CPC ....... *G01N 33/5748* (2013.01); *A61K 31/277* (2013.01); *A61K 31/553* (2013.01); *C12Q 1/6886* (2013.01); *G01N 33/5017* (2013.01); *G01N 33/5023* (2013.01); *G01N 33/57419* (2013.01); *G01N 33/57446* (2013.01); *C12Q 2600/136* (2013.01); *C12Q 2600/156* (2013.01); *C12Q 2600/16* (2013.01); *G01N 2500/00* (2013.01)

(58) Field of Classification Search
None
See application file for complete search history.

(56) References Cited

FOREIGN PATENT DOCUMENTS

| JP | 4303303 | 7/2009 |
| WO | 2011/162295 | 12/2011 |

OTHER PUBLICATIONS

Buccoliero et al. Congenital/infantile fibrosarcoma of the colon. J Pediatr Hematol Oncol., vol. 30, p. 723-727, 2008.*
Knezevich et al. A novel ETV6-NTRK3 gene fusion in congenital fibrosarcoma. Nature Genetics, vol. 18, p. 184-187, 1998.*
Luo et al. NTRK3 is a potential tumor suppressor gene commonly inactivated by epigenetic mechanisms in colorectal cancer. PLOS genetics, vol. 9(7), e1003552, p. 1-14, 2013.*
Wielenga et al. Expression of CD44 variant proteins in human colorectal cancer is related to tumor progression. Cancer Research, vol. 53, p. 4754-4756, 1993.*
Seshagiri et al., Recurrent R-spondin fusions in colon cancer, Nature 2012;488(7413):660-4.*
Kloosterman et al., A systematic analysis of oncogenic gene fusions in primary colon cancer, Cancer Res. Jul. 15, 2017;77(14):3814-3822. doi: 10.1158/0008-5472.CAN-16-3563. Epub May 16, 2017.*
Lugo et. al., "Tyrosine Kinase Activity and Transformation Potency of bcr-abl Oncogene Products." Department of Microbiology and Molecular Biology Institute and the Howard Hughes Medical Institute, University of California, Los Angeles, CA 90024. (1990).
Lamballe et. al., "The trk Family of Oncogenes and Neurotrophin Receptors" Department of Molecular Biology, Bristol-Myers Squibb Pharmaceutical Research Institute, Princeton, New Jersey 08543-4000, USA. 133-170. (1992).
Hatta Y. et. al., Ovarian cancer has frequent loss of heterozygosity at chromosome 12p12.3-13.1 (region of TEL and Kip1 loci) and chromsome 12q23-ter: evidence for two new tumour-suppressor genes., Br. J Cancer., vol. 75, No. 9, pp. 1256-1262. (1997).
Knezevich et. al., "A novel ETV6-NTRK3 gene fusion in congenital fibrosarcoma." Nature Publishing Group. (1998), Nature Genetics, vol. 18, p. 184-187.
Knezevish et. al., "*Homo sapiens* ETS related protein-growth factor receptor tyrosine kinase fusion proteins (ETV6-NTRK3 fusion) mRNA, partial cds." National GenBank. 184-187. (1998).
Wai et. al., "The ETV6-NTRK3 gene fusion encodes a chimeric protein tyrosine kinase that transforms NIH3T3 cells." Oncogane 19, 906-915. (2000).
Hisaoka et. al., "Gene Expression of TrkC (NTRK3) in human soft tissue tumours." Journal of Pathology. J Pathol; 197; 661-667. (2002).
Tognon, et. al., "Expression of the ETV6-NTRK3 gene fusion as a primary event in human secretory breast carcinoma." Cancer Cell. vol. 2. (2002).
Kinoshita et. al., "Chimera Idenshi Kaiseki ga Kakutei Shindan ni Yuko de atta Nanbu Shuyo No. 2 Rei." Pediatric Oncology, vol. 40, No. 3, p. 407, O-5-3. (2003).
Lannon et. al., "ETV6-NTRK3: a chimeric protein tyrosine kinase with transformation activity in multiple cell lineages." Seminars in Cancer Biology 15, 215-223. (2005).

(Continued)

*Primary Examiner* — Aaron A Priest
(74) *Attorney, Agent, or Firm* — Heslin Rothenberg Farley & Mesiti P.C.

(57) ABSTRACT

A polynucleotide, which is a novel causative gene for cancer, is elucidated, and, based on this finding, provided are a method for detecting the polynucleotide, or a polypeptide encoded by the polynucleotide; a kit and a primer set for the detection; a method for screening an inhibitor of the polypeptide; and a pharmaceutical composition for treating a cancer containing the inhibitor. In the detection method of the present invention, an NTRK3 fusion protein, or a fusion gene encoding the fusion protein, or an ETV6 fusion protein, or a fusion gene encoding the fusion protein, in a sample derived from the digestive system obtained from a subject, is detected.

3 Claims, No Drawings
Specification includes a Sequence Listing.

(56) References Cited

OTHER PUBLICATIONS

Edited by Ishikawa et. al., "Seibutsugaku Jiten," 1st Edition, Kabushiki Kaisha Toyko Kagaku Dojin, p. 619. (2010).
Kratochvil, et. al., "Mammary analog secretory carcinoma of salivary glands: a report of 2 cases in the lips." Oregon Health and Science University. Portland, Oregon. vol. 114 No. 5. (2012).
Laco et. al, "Mammary analog secretory carcinoma of salivary glands: A report of 2 cases with expression of basal/myoepithelial markers (calponin, CD10 and p63 protein)." Pathology—Research and Practice 209, 167-172. (2013).
Sakata et. al., "Fusion Gene in Epithelial Tumors." The Cell, vol. 45, No. 2, pp. 101-103. (2013).
International Search Report, PCT/JP2014/069737, dated Oct. 21, 2014, pp. 1-5.
Written Opinion of the International Searching Authority, PCTJP2014/069737, dated Oct. 28, 2014, pp. 1-12.
Buccolerio et al., 2002, Congenital/Infantile Fibrosarcoma of the Colon, J. Pediatr. Hematol. Oncol., 30:723-727.

* cited by examiner

SEQUENCE LISTING

<160> NUMBER OF SEQ ID NOS: 5

<210> SEQ ID NO 1
<211> LENGTH: 1902
<212> TYPE: DNA
<213> ORGANISM: Homo sapiens
<220> FEATURE:
<221> NAME/KEY: CDS
<222> LOCATION: (1)..(1902)

<400> SEQUENCE: 1

| | | | | | | | | | | | | | | | | |
|---|---|---|---|---|---|---|---|---|---|---|---|---|---|---|---|---|
| atg | tct | gag | act | cct | gct | cag | tgt | agc | att | aag | cag | gaa | cga | att | tca | 48 |
| Met | Ser | Glu | Thr | Pro | Ala | Gln | Cys | Ser | Ile | Lys | Gln | Glu | Arg | Ile | Ser | |
| 1 | | | | 5 | | | | | 10 | | | | | 15 | | |

| tat | aca | cct | cca | gag | agc | cca | gtg | ccg | agt | tac | gct | tcc | tcg | acg | cca | 96 |
|---|---|---|---|---|---|---|---|---|---|---|---|---|---|---|---|---|
| Tyr | Thr | Pro | Pro | Glu | Ser | Pro | Val | Pro | Ser | Tyr | Ala | Ser | Ser | Thr | Pro | |
| | | | 20 | | | | | 25 | | | | | 30 | | | |

| ctt | cat | gtt | cca | gtg | cct | cga | gcg | ctc | agg | atg | gag | gaa | gac | tcg | atc | 144 |
|---|---|---|---|---|---|---|---|---|---|---|---|---|---|---|---|---|
| Leu | His | Val | Pro | Val | Pro | Arg | Ala | Leu | Arg | Met | Glu | Glu | Asp | Ser | Ile | |
| | | 35 | | | | | 40 | | | | | 45 | | | | |

| cgc | ctg | cct | gcg | cac | ctg | cgc | ttg | cag | cca | att | tac | tgg | agc | agg | gat | 192 |
|---|---|---|---|---|---|---|---|---|---|---|---|---|---|---|---|---|
| Arg | Leu | Pro | Ala | His | Leu | Arg | Leu | Gln | Pro | Ile | Tyr | Trp | Ser | Arg | Asp | |
| 50 | | | | | 55 | | | | | 60 | | | | | | |

| gac | gta | gcc | cag | tgg | ctc | aag | tgg | gct | gaa | aat | gag | ttt | tct | tta | agg | 240 |
|---|---|---|---|---|---|---|---|---|---|---|---|---|---|---|---|---|
| Asp | Val | Ala | Gln | Trp | Leu | Lys | Trp | Ala | Glu | Asn | Glu | Phe | Ser | Leu | Arg | |
| 65 | | | | | 70 | | | | | 75 | | | | | 80 | |

| cca | att | gac | agc | aac | acg | ttt | gaa | atg | aat | ggc | aaa | gct | ctc | ctg | ctg | 288 |
|---|---|---|---|---|---|---|---|---|---|---|---|---|---|---|---|---|
| Pro | Ile | Asp | Ser | Asn | Thr | Phe | Glu | Met | Asn | Gly | Lys | Ala | Leu | Leu | Leu | |
| | | | | 85 | | | | | 90 | | | | | 95 | | |

| ctg | acc | aaa | gag | gac | ttt | cgc | tat | cga | tct | cct | cat | tca | ggt | gat | gtg | 336 |
|---|---|---|---|---|---|---|---|---|---|---|---|---|---|---|---|---|
| Leu | Thr | Lys | Glu | Asp | Phe | Arg | Tyr | Arg | Ser | Pro | His | Ser | Gly | Asp | Val | |
| | | | 100 | | | | | 105 | | | | | 110 | | | |

| ctc | tat | gaa | ctc | ctt | cag | cat | att | ctg | aag | cag | agg | aaa | cct | cgg | att | 384 |
|---|---|---|---|---|---|---|---|---|---|---|---|---|---|---|---|---|
| Leu | Tyr | Glu | Leu | Leu | Gln | His | Ile | Leu | Lys | Gln | Arg | Lys | Pro | Arg | Ile | |
| | | 115 | | | | | 120 | | | | | 125 | | | | |

| ctt | ttt | tca | cca | ttc | ttc | cac | cct | gga | aac | tct | ata | cac | aca | cag | ccg | 432 |
|---|---|---|---|---|---|---|---|---|---|---|---|---|---|---|---|---|
| Leu | Phe | Ser | Pro | Phe | Phe | His | Pro | Gly | Asn | Ser | Ile | His | Thr | Gln | Pro | |
| 130 | | | | | 135 | | | | | 140 | | | | | | |

| gag | gtc | ata | ctg | cat | cag | aac | cat | gaa | gaa | gat | aac | tgt | gtc | cag | agg | 480 |
|---|---|---|---|---|---|---|---|---|---|---|---|---|---|---|---|---|
| Glu | Val | Ile | Leu | His | Gln | Asn | His | Glu | Glu | Asp | Asn | Cys | Val | Gln | Arg | |
| 145 | | | | | 150 | | | | | 155 | | | | | 160 | |

| acc | ccc | agg | cca | tcc | gtg | gat | aat | gtg | cac | cat | aac | cct | ccc | acc | att | 528 |
|---|---|---|---|---|---|---|---|---|---|---|---|---|---|---|---|---|
| Thr | Pro | Arg | Pro | Ser | Val | Asp | Asn | Val | His | His | Asn | Pro | Pro | Thr | Ile | |
| | | | | 165 | | | | | 170 | | | | | 175 | | |

| gaa | ctg | ttg | cac | cgc | tcc | agg | tca | cct | atc | acg | aca | aat | cac | cgg | cct | 576 |
|---|---|---|---|---|---|---|---|---|---|---|---|---|---|---|---|---|
| Glu | Leu | Leu | His | Arg | Ser | Arg | Ser | Pro | Ile | Thr | Thr | Asn | His | Arg | Pro | |
| | | | 180 | | | | | 185 | | | | | 190 | | | |

| tct | cct | gac | ccc | gag | cag | cgg | ccc | ctc | cgg | tcc | ccc | ctg | gac | aac | atg | 624 |
|---|---|---|---|---|---|---|---|---|---|---|---|---|---|---|---|---|
| Ser | Pro | Asp | Pro | Glu | Gln | Arg | Pro | Leu | Arg | Ser | Pro | Leu | Asp | Asn | Met | |
| | | 195 | | | | | 200 | | | | | 205 | | | | |

| atc | cgc | cgc | ctc | tcc | ccg | gct | gag | aga | gct | cag | gga | ccc | agg | ccg | cac | 672 |
|---|---|---|---|---|---|---|---|---|---|---|---|---|---|---|---|---|
| Ile | Arg | Arg | Leu | Ser | Pro | Ala | Glu | Arg | Ala | Gln | Gly | Pro | Arg | Pro | His | |
| | 210 | | | | | 215 | | | | | 220 | | | | | |

| cag | gag | aac | aac | cac | cag | gag | tcc | tac | cct | ctg | tca | gtg | tct | ccc | atg | 720 |
|---|---|---|---|---|---|---|---|---|---|---|---|---|---|---|---|---|
| Gln | Glu | Asn | Asn | His | Gln | Glu | Ser | Tyr | Pro | Leu | Ser | Val | Ser | Pro | Met | |
| 225 | | | | | 230 | | | | | 235 | | | | | 240 | |

| gag | aat | aat | cac | tgc | cca | gcg | tcc | tcc | gag | tcc | cac | ccg | aag | cca | tcc | 768 |
|---|---|---|---|---|---|---|---|---|---|---|---|---|---|---|---|---|
| Glu | Asn | Asn | His | Cys | Pro | Ala | Ser | Ser | Glu | Ser | His | Pro | Lys | Pro | Ser | |
| | | | | 245 | | | | | 250 | | | | | 255 | | |

| agc | ccc | cgg | cag | gag | agc | aca | cgc | gtg | atc | cag | ctg | atg | ccc | agc | ccc | 816 |
|---|---|---|---|---|---|---|---|---|---|---|---|---|---|---|---|---|
| Ser | Pro | Arg | Gln | Glu | Ser | Thr | Arg | Val | Ile | Gln | Leu | Met | Pro | Ser | Pro | |

```
                260               265               270
atc atg cac cct ctg atc ctg aac ccc cgg cac tcc gtg gat ttc aaa    864
Ile Met His Pro Leu Ile Leu Asn Pro Arg His Ser Val Asp Phe Lys
        275               280               285 cag tcc agg ctc tcc gag gac ggg ctg cat agg gaa ggg aag ccc atc    912
Gln Ser Arg Leu Ser Glu Asp Gly Leu His Arg Glu Gly Lys Pro Ile
    290               295               300 aac ctc tct cat cgg gaa gac ctg gct tac atg aac cac atc atg gtc    960
Asn Leu Ser His Arg Glu Asp Leu Ala Tyr Met Asn His Ile Met Val
305               310               315               320 tct gtc tcc ccg cct gaa gag cac gcc atg ccc att ggg aga ata gca   1008
Ser Val Ser Pro Pro Glu Glu His Ala Met Pro Ile Gly Arg Ile Ala
            325               330               335 gat gtg cag cac att aag agg aga gac atc gtg ctg aag cga gaa ctg   1056
Asp Val Gln His Ile Lys Arg Arg Asp Ile Val Leu Lys Arg Glu Leu
        340               345               350 ggt gag gga gcc ttt gga aag gtc ttc ctg gcc gag tgc tac aac ctc   1104
Gly Glu Gly Ala Phe Gly Lys Val Phe Leu Ala Glu Cys Tyr Asn Leu
    355               360               365 agc ccg acc aag gac aag atg ctt gtg gct gtg aag gcc ctg aag gat   1152
Ser Pro Thr Lys Asp Lys Met Leu Val Ala Val Lys Ala Leu Lys Asp
370               375               380 ccc acc ctg gct gcc cgg aag gat ttc cag agg gag gcc gag ctg ctc   1200
Pro Thr Leu Ala Ala Arg Lys Asp Phe Gln Arg Glu Ala Glu Leu Leu
385               390               395               400 acc aac ctg cag cat gag cac att gtc aag ttc tat gga gtg tgc ggc   1248
Thr Asn Leu Gln His Glu His Ile Val Lys Phe Tyr Gly Val Cys Gly
            405               410               415 gat ggg gac ccc ctc atc atg gtc ttt gaa tac atg aag cat gga gac   1296
Asp Gly Asp Pro Leu Ile Met Val Phe Glu Tyr Met Lys His Gly Asp
        420               425               430 ctg aat aag ttc ctc agg gcc cat ggg cca gat gca atg atc ctt gtg   1344
Leu Asn Lys Phe Leu Arg Ala His Gly Pro Asp Ala Met Ile Leu Val
    435               440               445 gat gga cag cca cgc cag gcc aag ggt gag ctg ggg ctc tcc caa atg   1392
Asp Gly Gln Pro Arg Gln Ala Lys Gly Glu Leu Gly Leu Ser Gln Met
450               455               460 ctc cac att gcc agt cag atc gcc tcg ggt atg gtg tac ctg gcc tcc   1440
Leu His Ile Ala Ser Gln Ile Ala Ser Gly Met Val Tyr Leu Ala Ser
465               470               475               480 cag cac ttt gtg cac cga gac ctg gcc acc agg aac tgc ctg gtt gga   1488
Gln His Phe Val His Arg Asp Leu Ala Thr Arg Asn Cys Leu Val Gly
            485               490               495 gcg aat ctg cta gtg aag att ggg gac ttc ggc atg tcc aga gat gtc   1536
Ala Asn Leu Leu Val Lys Ile Gly Asp Phe Gly Met Ser Arg Asp Val
        500               505               510 tac agc acg gat tat tac agg gtg gga gga cac acc atg ctc ccc att   1584
Tyr Ser Thr Asp Tyr Tyr Arg Val Gly Gly His Thr Met Leu Pro Ile
    515               520               525 cgc tgg atg cct cct gaa agc atc atg tac cgg aag ttc act aca gag   1632
Arg Trp Met Pro Pro Glu Ser Ile Met Tyr Arg Lys Phe Thr Thr Glu
530               535               540 agt gat gta tgg agc ttc ggg gtg atc ctc tgg gag atc ttc acc tat   1680
Ser Asp Val Trp Ser Phe Gly Val Ile Leu Trp Glu Ile Phe Thr Tyr
545               550               555               560 gga aag cag cca tgg ttc caa ctc tca aac acg gag gtc att gag tgc   1728
Gly Lys Gln Pro Trp Phe Gln Leu Ser Asn Thr Glu Val Ile Glu Cys
            565               570               575 att acc caa ggt cgt gtt ttg gag cgg ccc cga gtc tgc ccc aaa gag   1776
```

-continued

```
Ile Thr Gln Gly Arg Val Leu Glu Arg Pro Arg Val Cys Pro Lys Glu
            580                 585                 590 gtg tac gat gtc atg ctg ggg tgc tgg cag agg gaa cca cag cag cgg    1824
Val Tyr Asp Val Met Leu Gly Cys Trp Gln Arg Glu Pro Gln Gln Arg
        595                 600                 605 ttg aac atc aag gag atc tac aaa atc ctc cat gct ttg ggg aag gcc    1872
Leu Asn Ile Lys Glu Ile Tyr Lys Ile Leu His Ala Leu Gly Lys Ala
610                 615                 620 acc cca atc tac ctg gac att ctt ggc tag                            1902
Thr Pro Ile Tyr Leu Asp Ile Leu Gly
625                 630

<210> SEQ ID NO 2
<211> LENGTH: 633
<212> TYPE: PRT
<213> ORGANISM: Homo sapiens

<400> SEQUENCE: 2

Met Ser Glu Thr Pro Ala Gln Cys Ser Ile Lys Gln Glu Arg Ile Ser
1               5                   10                  15

Tyr Thr Pro Pro Glu Ser Pro Val Pro Ser Tyr Ala Ser Ser Thr Pro
            20                  25                  30

Leu His Val Pro Val Pro Arg Ala Leu Arg Met Glu Glu Asp Ser Ile
        35                  40                  45

Arg Leu Pro Ala His Leu Arg Leu Gln Pro Ile Tyr Trp Ser Arg Asp
    50                  55                  60

Asp Val Ala Gln Trp Leu Lys Trp Ala Glu Asn Glu Phe Ser Leu Arg
65                  70                  75                  80

Pro Ile Asp Ser Asn Thr Phe Glu Met Asn Gly Lys Ala Leu Leu Leu
                85                  90                  95

Leu Thr Lys Glu Asp Phe Arg Tyr Arg Ser Pro His Ser Gly Asp Val
            100                 105                 110

Leu Tyr Glu Leu Leu Gln His Ile Leu Lys Gln Arg Lys Pro Arg Ile
        115                 120                 125

Leu Phe Ser Pro Phe Phe His Pro Gly Asn Ser Ile His Thr Gln Pro
    130                 135                 140

Glu Val Ile Leu His Gln Asn His Glu Glu Asp Asn Cys Val Gln Arg
145                 150                 155                 160

Thr Pro Arg Pro Ser Val Asp Asn Val His His Asn Pro Pro Thr Ile
                165                 170                 175

Glu Leu Leu His Arg Ser Arg Ser Pro Ile Thr Thr Asn His Arg Pro
            180                 185                 190

Ser Pro Asp Pro Glu Gln Arg Pro Leu Arg Ser Pro Leu Asp Asn Met
        195                 200                 205

Ile Arg Arg Leu Ser Pro Ala Glu Arg Ala Gln Gly Pro Arg Pro His
    210                 215                 220

Gln Glu Asn Asn His Gln Glu Ser Tyr Pro Leu Ser Val Ser Pro Met
225                 230                 235                 240

Glu Asn Asn His Cys Pro Ala Ser Ser Glu Ser His Pro Lys Pro Ser
                245                 250                 255

Ser Pro Arg Gln Glu Ser Thr Arg Val Ile Gln Leu Met Pro Ser Pro
            260                 265                 270

Ile Met His Pro Leu Ile Leu Asn Pro Arg His Ser Val Asp Phe Lys
        275                 280                 285

Gln Ser Arg Leu Ser Glu Asp Gly Leu His Arg Glu Gly Lys Pro Ile
    290                 295                 300
```

Asn Leu Ser His Arg Glu Asp Leu Ala Tyr Met Asn His Ile Met Val
305                 310                 315                 320

Ser Val Ser Pro Pro Glu His Ala Met Pro Ile Gly Arg Ile Ala
            325                 330                 335

Asp Val Gln His Ile Lys Arg Arg Asp Ile Val Leu Lys Arg Glu Leu
                340                 345                 350

Gly Glu Gly Ala Phe Gly Lys Val Phe Leu Ala Glu Cys Tyr Asn Leu
                355                 360                 365

Ser Pro Thr Lys Asp Lys Met Leu Val Ala Val Lys Ala Leu Lys Asp
    370                 375                 380

Pro Thr Leu Ala Ala Arg Lys Asp Phe Gln Arg Glu Ala Glu Leu Leu
385                 390                 395                 400

Thr Asn Leu Gln His Glu His Ile Val Lys Phe Tyr Gly Val Cys Gly
                405                 410                 415

Asp Gly Asp Pro Leu Ile Met Val Phe Glu Tyr Met Lys His Gly Asp
                420                 425                 430

Leu Asn Lys Phe Leu Arg Ala His Gly Pro Asp Ala Met Ile Leu Val
            435                 440                 445

Asp Gly Gln Pro Arg Gln Ala Lys Gly Glu Leu Gly Leu Ser Gln Met
450                 455                 460

Leu His Ile Ala Ser Gln Ile Ala Ser Gly Met Val Tyr Leu Ala Ser
465                 470                 475                 480

Gln His Phe Val His Arg Asp Leu Ala Thr Arg Asn Cys Leu Val Gly
                485                 490                 495

Ala Asn Leu Leu Val Lys Ile Gly Asp Phe Gly Met Ser Arg Asp Val
            500                 505                 510

Tyr Ser Thr Asp Tyr Tyr Arg Val Gly Gly His Thr Met Leu Pro Ile
            515                 520                 525

Arg Trp Met Pro Pro Glu Ser Ile Met Tyr Arg Lys Phe Thr Thr Glu
            530                 535                 540

Ser Asp Val Trp Ser Phe Gly Val Ile Leu Trp Glu Ile Phe Thr Tyr
545                 550                 555                 560

Gly Lys Gln Pro Trp Phe Gln Leu Ser Asn Thr Glu Val Ile Glu Cys
                565                 570                 575

Ile Thr Gln Gly Arg Val Leu Glu Arg Pro Arg Val Cys Pro Lys Glu
                580                 585                 590

Val Tyr Asp Val Met Leu Gly Cys Trp Gln Arg Glu Pro Gln Gln Arg
            595                 600                 605

Leu Asn Ile Lys Glu Ile Tyr Lys Ile Leu His Ala Leu Gly Lys Ala
            610                 615                 620

Thr Pro Ile Tyr Leu Asp Ile Leu Gly
625                 630

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: synthetic
      primer

<400> SEQUENCE: 3
gaagcccatc aacctctctc atcgg                                          25

<210> SEQ ID NO 4

```
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4
agccggaggt catactgcat                                                   20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 5
cagttctcgc ttcagcacg                                                    19
```

DETECTION METHOD FOR NTRK3 FUSION

CROSS REFERENCE TO RELATED APPLICATIONS

This application is a national stage of PCT International Application No. PCT/JP2014/069737, filed on Jul. 25, 2014, and published in Japanese on Jan. 29, 2015 as WO 2015/012397 A1, the entire disclosure of which is incorporated herein by reference.

TECHNICAL FIELD

The present invention relates to a method for detecting a fusion protein comprising an NTRK3 kinase region, or a fusion gene encoding the fusion protein.

The present invention relates to a method for detecting a fusion protein comprising at least a portion of an ETV6 protein, or a fusion gene encoding the fusion protein.

BACKGROUND ART

As a result of chromosomal translocation, originally separate genes fuse into a fusion gene. It is known that fusion genes containing part of a kinase gene, such as a BCR-ABL1 fusion in chronic myelogenous leukemia, an EML4-ALK fusion in lung cancer, and an ROS1 fusion in a variety of cancers including lung cancer, often play an essential role in carcinogenesis, and that drugs which inhibit the function become an extremely effective anti-cancer agent (Non-patent literature 1, and patent literatures 1 and 2).

Nowadays, the relationship between molecular diagnosis and therapeutic effects on cancer is being shown clinically by the appearance of, for example, tyrosine kinase inhibitors Iressa and Tarceva. As a result, the concept of drug administration to eligible patients stratified by molecular diagnosis is spreading.

With respect to an ETV6 (Ets Variant6)-NTRK3 (Neutrophic Tyrosine Kinase, Receptor, Type3) fusion, its presence was reported in sarcoma (Non-patent literature 2) and breast carcinoma (Non-patent literature 3), but there has been no report in digestive system cancer. There has been no report that a kinase domain of NTRK3 can be part of a fusion (i.e., the presence of a fusion containing the kinase domain of NTRK3) in digestive system cancer (Non-patent literature 4).

CITATION LIST

Patent Literature

[Patent literature 1] Japanese Patent No. 4303303
[Patent literature 2] WO2011/162295

Non-Patent Literature

[Non-patent literature 1] Lugo T G, Pendergast A M, Muller A J, Witte O N. Tyrosine kinase activity and transformation potency of bcr-abl oncogene products. Science. 1990 Mar. 2; 247(4946): 1079-1082
[Non-patent literature 2] Knezevich S R, McFadden D E, Tao W, Lim J F, Sorensen P H. A novel ETV6-NTRK3 gene fusion in congenital fibrosarcoma. Nat Genet. 1998 February; 18(2): 184-7
[Non-patent literature 3] Tognon C, Knezevich S R, Huntsman D, Roskelley C D, Melnyk N, Mathers J A, Becker L, Carneiro F, MacPherson N, Horsman D, Poremba C, Sorensen P H. Expression of the ETV6-NTRK3 gene fusion as a primary event in human secretory breast carcinoma. Cancer Cell. 2002 November; 2(5): 367-76
[Non-patent literature 4] Hisaoka M, Sheng W Q, Tanaka A, Hashimoto H. Gene expression of TrkC (NTRK3) in human soft tissue tumours. J Pathol. 2002 August; 197(5): 661-67

SUMMARY OF INVENTION

Technical Problem

An object of the present invention is to elucidate a polynucleotide, which is a novel causative gene for cancer, and, based on this finding, to provide a method for detecting the polynucleotide, or a polypeptide encoded by the polynucleotide; a kit and a primer set for the detection; a method for screening an inhibitor of the polypeptide; and a pharmaceutical composition for treating a cancer containing the inhibitor, and a method for treating a cancer by administering the pharmaceutical composition for treating the cancer.

Solution to Problem

The inventors of the present invention confirmed the fusion of part of an ETV6 gene and part of an NTRK3 gene, which was a kinase, in a specimen obtained from a patient with colon cancer (Example 2), and found that the fusion gene was present in the specimen from the patient with colon cancer (Examples 3 and 4).

From these findings, the inventors of the present invention constructed a method of detecting the NTRK3 fusion gene, or a fusion protein encoded by the fusion gene (Examples 3-5), and provided a kit and a primer set for the detection method, and made it possible to select cancer patients to be treated with an NTRK3 inhibitor by detecting the fusion gene, or the fusion protein encoded by the fusion gene.

From these findings, the inventors of the present invention constructed a method of detecting the ETV6 fusion gene, or a fusion protein encoded by the fusion gene (Examples 3-5), and provided a kit and a primer set for the detection method, and made it possible to select cancer patients to be treated with an ETV6 inhibitor by detecting the fusion gene, or the fusion protein encoded by the fusion gene.

The present invention relates to the following inventions:

[1] A method for detecting an NTRK3 fusion protein, or a fusion gene encoding the fusion protein in a sample derived from the digestive system obtained from a subject.

[2] The method of [1], comprising a step of detecting the cleavage of an NTRK3 protein, or the cleavage of a gene encoding the NTRK3 protein.

[3] The method of [1], comprising a step of detecting the presence of a fusion protein constructed from an NTRK3 protein and a protein other than the NTRK3 protein, or the presence of a fusion gene encoding the fusion protein.

[4] The method of any one of [1] to [3], wherein the fusion protein is a fusion protein of an ETV6 protein and an NTRK3 protein.

[5] The method of any one of [1] to [4], wherein the fusion protein is a polypeptide selected from the group consisting of the following (a) to (d):

(a) a polypeptide consisting of the amino acid sequence of SEQ ID NO: 2, (b) a polypeptide with oncogenic potential comprising the amino acid sequence of SEQ ID NO: 2, (c) a polypeptide with oncogenic potential comprising an amino acid sequence that has at least 80% identity to the amino acid sequence of SEQ ID NO: 2, and (d) a polypeptide with oncogenic potential comprising an amino acid sequence in which one or several amino acids are deleted, substituted, and/or inserted in the amino acid sequence of SEQ ID NO: 2.

[6] The method of any one of [1] to [5], wherein the NTRK3 fusion gene is a polynucleotide encoding the polypeptide described in [5].

[7] The method of any one of [1] to [6], wherein the fusion gene is DNA or mRNA.

[8] The method of any one of [1] to [7], wherein the digestive system is the digestive tract.

[9] The method of any one of [1] to [7], wherein the digestive system is the lower digestive tract.

[10] The method of any one of [1] to [7], wherein the digestive system is the large intestine.

[11] A kit for detecting an NTRK3 fusion gene, comprising one probe capable of specifically recognizing a genomic region at the 5' terminus of an NTRK3 gene, and another probe capable of specifically recognizing a genomic region at the 3' terminus of the NTRK3 gene.

[12] A kit for detecting an NTRK3 fusion gene, comprising one probe capable of specifically recognizing a genomic region at the 5' terminus of a gene that constitutes an NTRK3 fusion gene together with an NTRK3 gene, and another probe capable of specifically recognizing a genomic region at the 3' terminus of the NTRK3 gene.

[13] A kit for detecting an NTRK3 fusion gene, comprising a sense primer and an antisense primer designed so as to specifically amplify a region at the 5' terminus of a polynucleotide encoding an NTRK3 protein, and a sense primer and an antisense primer designed so as to specifically amplify a region at the 3' terminus of the polynucleotide.

[14] A kit for detecting an NTRK3 fusion gene, comprising a sense primer and an antisense primer designed so as to specifically amplify a polynucleotide encoding a polypeptide, which is a fusion protein of an ETV6 protein and an NTRK3 protein.

[15] A kit for detecting an NTRK3 fusion gene, comprising a sense primer and an antisense primer designed so as to specifically amplify a polynucleotide encoding a polypeptide selected from the group consisting of the following (a) to (d):

(a) a polypeptide consisting of the amino acid sequence of SEQ ID NO: 2, (b) a polypeptide with oncogenic potential comprising the amino acid sequence of SEQ ID NO: 2, (c) a polypeptide with oncogenic potential comprising an amino acid sequence that has at least 80% identity to the amino acid sequence of SEQ ID NO: 2, and (d) a polypeptide with oncogenic potential comprising an amino acid sequence in which one or several amino acids are deleted, substituted, and/or inserted in the amino acid sequence of SEQ ID NO: 2.

[16] A kit for detecting an NTRK3 fusion protein, comprising an anti-NTRK3 antibody capable of specifically recognizing an N-terminal region of an NTRK3 protein, and an anti-NTRK3 antibody capable of specifically recognizing a C-terminal region of the NTRK3 protein.

[17] A kit for detecting an NTRK3 fusion protein, comprising an antibody which specifically binds to a polypeptide of an N-terminal region of a protein which constitutes an NTRK3 fusion protein together with an NTRK3 protein, and an antibody which specifically binds to a polypeptide of a C-terminal region of the NTRK3 protein.

[18] The kit of [17], wherein the protein which constitutes an NTRK3 fusion protein together with an NTRK3 protein is an ETV6 protein.

[19] A primer set for detecting a fusion gene of an ETV6 gene and an NTRK3 gene, comprising a sense primer designed from a polynucleotide portion encoding an ETV6 protein, and an antisense primer designed from a polynucleotide portion encoding an NTRK3 protein, wherein the antisense primer consists of a nucleic acid molecule which anneals to the polynucleotide described in [15] under stringent conditions, and the sense primer consists of a nucleic acid molecule which anneals to a complementary strand to the polynucleotide described in [15] under stringent conditions.

[20] A primer set for detecting a fusion gene of an ETV6 gene and an NTRK3 gene, comprising an antisense primer consisting of a nucleic acid molecule which anneals to a polynucleotide consisting of the nucleotide sequence of SEQ ID NO: 1 under stringent conditions, and a sense primer consisting of a nucleic acid molecule which anneals to a complementary strand to the polynucleotide under stringent conditions.

[21] A primer set comprising a sense primer, which is an oligonucleotide consisting of at least 16 consecutive nucleotides in the region of nucleotides 1-1009 of SEQ ID NO: 1, and an antisense primer, which is an oligonucleotide complementary to an oligonucleotide consisting of at least 16 consecutive nucleotides in the region of nucleotides 1010-1902 of SEQ ID NO: 1.

[22] A method for screening a substance which inhibits the activity and/or the expression of the polypeptide described in [5], the method comprising:

(1) bringing a test substance into contact with the polypeptide, or a cell expressing the polypeptide, (2) analyzing whether or not the activity and/or the expression of the polypeptide is inhibited, and (3) selecting a substance which inhibits the activity and/or the expression of the polypeptide.

[23] The method of [22], wherein the substance which inhibits the activity and/or the expression of the polypeptide is a therapeutic agent for an NTRK3 fusion-positive cancer.

[24] The method of [22] or [23], wherein the cancer is a digestive system cancer.

[25] The method of [22] or [23], wherein the cancer is a digestive tract cancer.

[26] The method of [22] or [23], wherein the cancer is a lower digestive tract cancer.

[27] The method of [22] or [23], wherein the cancer is a colorectal cancer.

[28] A pharmaceutical composition for treating an NTRK3 fusion-positive cancer, comprising a substance which inhibits the activity and/or the expression of an NTRK3 fusion protein.

[29] The pharmaceutical composition of [28], wherein the substance which inhibits the activity and/or the expression of an NTRK3 fusion protein is a kinase inhibitor.

[30] The pharmaceutical composition of [28] or [29], wherein the NTRK3 fusion protein is the polypeptide described in [5].

[31] The pharmaceutical composition of any one of [28] to [30], wherein the cancer is a digestive system cancer.

[32] The pharmaceutical composition of any one of [28] to [30], wherein the cancer is a digestive tract cancer.

[33] The pharmaceutical composition of any one of [28] to [30], wherein the cancer is a lower digestive tract cancer.

[34] The pharmaceutical composition of any one of [28] to [30], wherein the cancer is a colorectal cancer.

[35] A method for treating a patient with cancer, comprising:
(1) determining the presence of an NTRK3 fusion protein, or a fusion gene encoding the fusion protein by the method of any one of [1] to [10], and
(2) based on the presence of the NTRK3 fusion protein, or the fusion gene encoding the fusion protein, treating the patient by administering thereto a pharmaceutical composition comprising a substance which inhibits the activity and/or the expression of an NTRK3 fusion protein.

[36] The method of [35], wherein the cancer is a digestive system cancer.

[37] The method of [35], wherein the cancer is a digestive tract cancer.

[38] The method of [35], wherein the cancer is a lower digestive tract cancer.

[39] The method of [35], wherein the cancer is a colorectal cancer.

[40] The method of any one of [35] to [39], wherein the substance which inhibits the activity and/or the expression of an NTRK3 fusion protein is a kinase inhibitor.

[41] Use of a substance which inhibits the activity and/or the expression of an NTRK3 fusion protein in the manufacture of a pharmaceutical composition for treating an NTRK3 fusion-positive cancer.

[42] A DNA encoding an NTRK3 fusion protein.

[43] A recombinant vector, wherein the DNA of [42] is inserted into a vector DNA.

[44] A transformed cell, wherein the recombinant vector of [43] is introduced.

[45] The DNA of [42], wherein the NTRK3 fusion protein is a fusion protein of an ETV6 protein and an NTRK3 protein.

[46] The DNA of [42], wherein the NTRK3 fusion protein is the fusion protein described in [5].

[47] The method of any one of [22] to [27], wherein the cell expressing the polypeptide is the transformed cell of [44].

[48] A method for detecting an ETV6 fusion protein, or a fusion gene encoding the fusion protein in a sample derived from the digestive system obtained from a subject.

[49] The method of [48], comprising a step of detecting the cleavage of an ETV6 protein, or the cleavage of a gene encoding the ETV6 protein.

[50] The method of [48], comprising a step of detecting the presence of a fusion protein constructed from an ETV6 protein and a protein other than the ETV6 protein, or the presence of a fusion gene encoding the fusion protein.

[51] The method of any one of [48] to [50], wherein the fusion protein is a fusion protein of an ETV6 protein and an NTRK3 protein.

[52] The method of any one of [48] to [51], wherein the fusion protein is a polypeptide selected from the group consisting of the following (a) to (d):
(a) a polypeptide consisting of the amino acid sequence of SEQ ID NO: 2,
(b) a polypeptide with oncogenic potential comprising the amino acid sequence of SEQ ID NO: 2,
(c) a polypeptide with oncogenic potential comprising an amino acid sequence that has at least 80% identity to the amino acid sequence of SEQ ID NO: 2, and
(d) a polypeptide with oncogenic potential comprising an amino acid sequence in which one or several amino acids are deleted, substituted, and/or inserted in the amino acid sequence of SEQ ID NO: 2.

[53] The method of any one of [48] to [52], wherein the ETV6 fusion gene is a polynucleotide encoding the polypeptide described in [52].

[54] The method of any one of [48] to [53], wherein the fusion gene is DNA or mRNA.

[55] The method of any one of [48] to [53], wherein the digestive system is the digestive tract.

[56] The method of any one of [48] to [53], wherein the digestive system is the lower digestive tract.

[57] The method of any one of [48] to [53], wherein the digestive system is the large intestine.

[58] A kit for detecting an ETV6 fusion gene, comprising one probe capable of specifically recognizing a genomic region at the 5' terminus of an ETV6 gene, and another probe capable of specifically recognizing a genomic region at the 3' terminus of the ETV6 gene.

[59] A kit for detecting an ETV6 fusion gene, comprising one probe capable of specifically recognizing a genomic region at the 3' terminus of a gene that constitutes an ETV6 fusion gene together with an ETV6 gene, and another probe capable of specifically recognizing a genomic region at the 5' terminus of the ETV6 gene.

[60] A kit for detecting an ETV6 fusion gene, comprising a sense primer and an antisense primer designed so as to specifically amplify a region at the 5' terminus of a polynucleotide encoding an ETV6 protein, and a sense primer and an antisense primer designed so as to specifically amplify a region at the 3' terminus of the polynucleotide.

[61] A kit for detecting an ETV6 fusion gene, comprising a sense primer and an antisense primer designed so as to specifically amplify a polynucleotide encoding a polypeptide which is a fusion protein of an ETV6 protein and an NTRK3 protein.

[62] A kit for detecting an ETV6 fusion gene, comprising a sense primer and an antisense primer designed so as to specifically amplify a polynucleotide encoding a polypeptide selected from the group consisting of the following (a) to (d):
(a) a polypeptide consisting of the amino acid sequence of SEQ ID NO: 2,
(b) a polypeptide with oncogenic potential comprising the amino acid sequence of SEQ ID NO: 2,
(c) a polypeptide with oncogenic potential comprising an amino acid sequence that has at least 80% identity to the amino acid sequence of SEQ ID NO: 2, and
(d) a polypeptide with oncogenic potential comprising an amino acid sequence in which one or several amino acids are deleted, substituted, and/or inserted in the amino acid sequence of SEQ ID NO: 2.

[63] A kit for detecting an ETV6 fusion protein, comprising an anti-ETV6 antibody capable of specifically recognizing an N-terminal region of an ETV6 protein, and an anti-ETV6 antibody capable of specifically recognizing a C-terminal region of the ETV6 protein.

[64] A kit for detecting an ETV6 fusion protein, comprising an antibody which specifically binds to a polypeptide of a C-terminal region of a protein which constitutes an ETV6 fusion protein together with an ETV6 protein, and an antibody which specifically binds to a polypeptide of an N-terminal region of the ETV6 protein.

[65] The kit of [64], wherein the protein which constitutes an NTRK3 fusion protein together with an NTRK3 protein is an NTRK3 protein.

[66] A primer set for detecting a fusion gene of an ETV6 gene and an NTRK3 gene, comprising a sense primer designed from a polynucleotide portion encoding an ETV6 protein, and an antisense primer designed from a polynucleotide portion encoding an NTRK3 protein, wherein the antisense primer consists of a nucleic acid molecule which anneals to the polynucleotide described in [62] under stringent conditions, and the sense primer consists of a nucleic acid molecule which anneals to a complementary strand to the polynucleotide described in [62] under stringent conditions.

[67] A primer set for detecting a fusion gene of an ETV6 gene and an NTRK3 gene, comprising an antisense primer consisting of a nucleic acid molecule which anneals to a polynucleotide consisting of the nucleotide sequence of SEQ ID NO: 1 under stringent conditions, and a sense primer consisting of a nucleic acid molecule which anneals to a complementary strand to the polynucleotide under stringent conditions.

[68] A primer set comprising a sense primer which is an oligonucleotide consisting of at least 16 consecutive nucleotides in the region of nucleotides 1-1009 of SEQ ID NO: 1, and an antisense primer which is an oligonucleotide complementary to an oligonucleotide consisting of at least 16 consecutive nucleotides in the region of nucleotides 1010-1902 of SEQ ID NO: 1.

[69] A method for screening a substance which inhibits the activity and/or the expression of the polypeptide described in [5], the method comprising:
(1) bringing a test substance into contact with the polypeptide, or a cell expressing the polypeptide,
(2) analyzing whether or not the activity and/or the expression of the polypeptide is inhibited, and
(3) selecting a substance which inhibits the activity and/or the expression of the polypeptide.

[70] The method of [69], wherein the substance which inhibits the activity and/or the expression of the polypeptide is a therapeutic agent for an ETV6 fusion-positive cancer.

[71] The method of [69] or [70], wherein the cancer is a digestive system cancer.

[72] The method of [69] or [70], wherein the cancer is a digestive tract cancer.

[73] The method of [69] or [70], wherein the cancer is a lower digestive tract cancer.

[74] The method of [69] or [70], wherein the cancer is a colorectal cancer.

[75] A pharmaceutical composition for treating an ETV6 fusion-positive cancer, comprising a substance which inhibits the activity and/or the expression of an ETV6 fusion protein.

[76] The pharmaceutical composition of [75], wherein the substance which inhibits the activity and/or the expression of an ETV6 fusion protein is a kinase inhibitor.

[77] The pharmaceutical composition of [75] or [76], wherein the ETV6 fusion protein is the polypeptide described in [5].

[78] The pharmaceutical composition of any one of [75] to [77], wherein the cancer is a digestive system cancer.

[79] The pharmaceutical composition of any one of [75] to [77], wherein the cancer is a digestive tract cancer.

[80] The pharmaceutical composition of any one of [75] to [77], wherein the cancer is a lower digestive tract cancer.

[81] The pharmaceutical composition of any one of [75] to [77], wherein the cancer is a colorectal cancer.

[82] A method for treating a patient with cancer, comprising:
(1) determining the presence of an ETV6 fusion protein, or a fusion gene encoding the fusion protein by the method of any one of [48] to [57], and
(2) based on the presence of the ETV6 fusion protein, or the fusion gene encoding the fusion protein, treating the patient by administering thereto a pharmaceutical composition comprising a substance which inhibits the activity and/or the expression of an ETV6 fusion protein.

[83] The method of [82], wherein the cancer is a digestive system cancer.

[84] The method of [82], wherein the cancer is a digestive tract cancer.

[85] The method of [82], wherein the cancer is a lower digestive tract cancer.

[86] The method of [82], wherein the cancer is a colorectal cancer.

[87] The method of any one of [82] to [86], wherein the substance which inhibits the activity and/or the expression of an ETV6 fusion protein is a kinase inhibitor.

[88] Use of a substance which inhibits the activity and/or the expression of an ETV6 fusion protein in the manufacture of a pharmaceutical composition for treating an ETV6 fusion-positive cancer.

Advantageous Effects of Invention

The detection method of the present invention can be used as a method for detecting an NTRK3 fusion-positive cancer (in particular, digestive system cancers). Further, it can be determined whether or not a patient is an application target for an NTRK3 inhibitor by the detection method of the present invention. The detection kit and the primer set of the present invention can be used in the detection method of the present invention. Further, drugs effective in the treatment of patients with the NTRK3 fusion-positive cancer can be screened by the inhibitor screening method of the present invention. The drugs obtained by the screening can be used as active ingredients of a pharmaceutical composition for treating the NTRK3 fusion-positive cancer, and can be used in treating the NTRK3 fusion-positive cancer. A cancer can be diagnosed using the present invention.

The detection method of the present invention can be used as a method for detecting an ETV6 fusion-positive cancer (in particular, digestive system cancers). Further, it can be determined whether or not a patient is an application target for an ETV6 inhibitor by the detection method of the present invention. The detection kit and the primer set of the present invention can be used in the detection method of the present invention. Further, drugs effective in the treatment of patients with the ETV6 fusion-positive cancer can be screened by the inhibitor screening method of the present invention. The drugs obtained by the screening can be used as active ingredients of a pharmaceutical composition for treating the ETV6 fusion-positive cancer, and can be used in treating the ETV6 fusion-positive cancer. A cancer can be diagnosed using the present invention.

DESCRIPTION OF EMBODIMENTS

Definitions and the Like

Fusion Point

The term "fusion point in an NTRK3 fusion gene" as used herein means a point in which a polynucleotide derived from the NTRK3 gene in the NTRK3 fusion gene is fused to a polynucleotide derived from a gene that constitutes the fusion gene together with the NTRK3 gene. For example, in the case of the fusion gene of SEQ ID NO: 1, the fusion point is a point in which the 1009th nucleotide of the nucleotide sequence is fused to the 1010th nucleotide thereof.

The term "fusion point in an NTRK3 fusion protein" as used herein means a point in which a polypeptide encoded by a polynucleotide derived from the NTRK3 gene in the NTRK3 fusion protein is fused to a polypeptide encoded by a polynucleotide derived from a gene that constitutes the fusion gene together with the NTRK3 gene.

The term "fusion point in an ETV6 fusion gene" as used herein means a point in which a polynucleotide derived from the ETV6 gene in the ETV6 fusion gene is fused to a polynucleotide derived from a gene that constitutes the fusion gene together with the ETV6 gene. For example, in the case of the fusion gene of SEQ ID NO: 1, the fusion point is a point in which the 1009th nucleotide of the nucleotide sequence is fused to the 1010th nucleotide thereof.

The term "fusion point in an ETV6 fusion protein" as used herein means a point in which a polypeptide encoded by a polynucleotide derived from the ETV6 gene in the ETV6 fusion protein is fused to a polypeptide encoded by a polynucleotide derived from a gene that constitutes the fusion gene together with the ETV6 gene.

Cleavage of NTRK3 Gene or NTRK3 Protein

The term "cleavage of an NTRK3 gene" or "an NTRK3 gene is cleaved" as used herein means a state in which the continuity of the NTRK3 gene is lost due to translocation, inversion, or the like of the gene, namely, a state in which the NTRK3 gene is separated into at least two polynucleotides, including a polynucleotide containing an NTRK3 kinase region and a polynucleotide containing other regions. The break point of the NTRK3 gene is not particularly limited, so long as a protein encoded by at least one polynucleotide generated by the cleavage of the NTRK3 gene maintains the NTRK3 kinase activity.

The term "cleavage of a gene other than NTRK3" or "a gene other than NTRK3 is cleaved" as used herein means a state in which the continuity of the gene other than NTRK3 (also called the other gene) is lost due to translocation, inversion, or the like of the gene, namely, a state in which the other gene is separated into at least two polynucleotides.

The term "cleavage of an NTRK3 protein" or "an NTRK3 protein is cleaved" as used herein means, based on the fact that the NTRK3 gene is cleaved as previously described, a state in which the continuity of the NTRK3 protein is lost, namely, a state in which the NTRK3 protein is separated into at least two polypeptides, including a polypeptide containing an NTRK3 kinase region and a polypeptide containing other regions. The break point of the NTRK3 protein is not particularly limited, so long as at least one protein generated by the cleavage of the NTRK3 protein maintains the NTRK3 kinase activity.

The term "cleavage of a protein other than NTRK3" or "a protein other than NTRK3 is cleaved" as used herein means, based on the fact that the other gene is cleaved as previously described, a state in which the continuity of the protein other than NTRK3 (also called the other protein) is lost, namely, a state in which the other protein is separated into at least two polypeptides.

Cleavage of ETV6 Gene or ETV6 Protein

The term "cleavage of an ETV6 gene" or "an ETV6 gene is cleaved" as used herein means a state in which the continuity of the ETV6 gene is lost due to translocation, inversion, or the like, of the gene. The break point of the ETV6 gene is not particularly limited, so long as a protein encoded by the other gene that constitutes the ETV6 fusion gene together with the ETV6 gene maintains its function (for example, when the protein has a kinase domain, the function is a kinase activity).

The term "cleavage of a gene other than an ETV6 gene" or "a gene other than an ETV6 gene is cleaved" as used herein means a state in which the continuity of the gene other than ETV6 (also called the other gene) is lost due to translocation, inversion, or the like of the gene, namely, a state in which the other gene is separated into at least two polynucleotides.

The term "cleavage of an ETV6 protein" or "an ETV6 protein is cleaved" as used herein means, based on the fact that the ETV6 gene is cleaved as previously described, a state in which the continuity of the ETV6 protein is lost, namely, a state in which the ETV6 protein is separated into at least two polypeptides. The break point of the ETV6 protein is not particularly limited, so long as the other protein that constitutes the ETV6 fusion protein together with the ETV6 protein maintains its function (for example, when the other protein has a kinase domain, the function is a kinase activity).

The term "cleavage of a protein other than an ETV6 protein" or "a protein other than an ETV6 protein is cleaved" as used herein means, based on the fact that the other gene is cleaved as previously described, a state in which the continuity of the protein other than ETV6 (also called the other protein) is lost, namely, a state in which the other protein is separated into at least two polypeptides.

5' Terminal Region/3' Terminal Region, and N-Terminal Region/C-Terminal Region

The term "5' terminal region" means, in the case of a fusion gene, a polynucleotide at the 5' terminal side from the fusion point, and in the case of a wild-type gene (a gene that is not a fusion gene), a polynucleotide at the 5' terminal side from the break point when the wild-type gene constitutes a fusion gene. The 5' terminal region may be genomic DNA, an mRNA, or a cDNA. For example, in the case of genomic DNA, the region is also called a 5' terminal genomic region.

The term "3' terminal region" means, in the case of a fusion gene, a polynucleotide at the 3' terminal side from the fusion point, and in the case of a wild-type gene (a gene that is not a fusion gene), a polynucleotide at the 3' terminal side from the break point when the wild-type gene constitutes a fusion gene. The 3' terminal region may be genomic DNA, an mRNA, or a cDNA. For example, in the case of genomic DNA, the region is also called a 3' terminal genomic region.

The term "N-terminal region" means, in the case of a fusion protein, a polypeptide at the N-terminal side from the fusion point, and in the case of a wild-type protein (a protein that is not a fusion protein), a polypeptide at the N-terminal side from the break point when the wild-type protein constitutes a fusion protein.

The term "C-terminal region" means, in the case of a fusion protein, a polypeptide at the C-terminal side from the fusion point, and in the case of a wild-type protein (a protein that is not a fusion protein), a polypeptide at the C-terminal side from the break point when the wild-type protein constitutes a fusion protein.

For example, in the case of the ETV6-NTRK3 fusion gene of SEQ ID NO: 1, the 5' terminal region is a polynucleotide consisting of nucleotides 1-1009, and the 3' terminal region is a polynucleotide consisting of nucleotides 1010-1653. In the case of the ETV6-NTRK3 fusion protein, the N-terminal region is a polypeptide encoded by the 5' terminal region, and the C-terminal region is a polypeptide encoded by the 3' terminal region.

cDNA Reference Sequences

As cDNA reference sequences of each original gene, ENST00000394480 for NTRK3, and ENST00000396373 for ETV6 are used, respectively. As amino acid reference sequences of each protein, ENSP00000377990 for NTRK3, and ENSP00000379658 for ETV6 are used, respectively.
Stringent Conditions The term "under stringent conditions" as used herein means that the hybridization is carried out in a solution containing 5×SSPE, 5×Denhardt's solution, 0.5% SDS, 50% formamide, and 200 μg/mL salmon sperm DNA at 42° C. overnight, and the washing is carried out in a solution containing 0.5×SSC and 0.1% SDS at 42° C. The term "under more stringent conditions" as used herein means that the hybridization is carried out in a solution containing 5×SSPE, 5×Denhardt's solution, 0.5% SDS, 50% formamide, and 200 g/mL salmon sperm DNA at 42° C. overnight, and that the washing is carried out in a solution containing 0.2×SSC and 0.1% SDS at 65° C.
Oncogenic Potential Whether or not a certain polypeptide has "oncogenic potential" can be confirmed by a known method, for example, a method described in Example 4 of WO2011/162295. More particularly, a nude mouse is subcutaneously inoculated with a host (3T3 fibroblast) into which a plasmid capable of expressing the polypeptide is introduced, and the oncogenic potential is confirmed by judging the presence or absence of tumor formation. With respect to the ETV6-NTRK3 fusion gene, transformation in transduced cells, and oncogenic potential in transduced-cell-transplanted mice were shown, and it is suggested that the presence of the fusion gene or its transcriptional product is a cause of cancer in the expression site (Wai D H et al., Oncogene. 2000 Feb. 17; 19(7): 906-915).
Sample in the Detection Method of the Present Invention
Target Organ The detection method of the present invention can be preferably used in the detection of cancer that occurs in the target organ. As a site to be analyzed (target organ) in the subject, the digestive system is preferable, the digestive tract is more preferable, the gastrointestinal tract is still more preferable, the lower digestive tract is still more preferable, and the large intestine is most preferable.

More particularly, the detection method of the present invention is used, preferably in the detection of digestive system cancer, more preferably in the detection of digestive tract cancer, still more preferably in the detection of gastrointestinal tract cancer, still more preferably in the detection of lower digestive tract cancer, and most preferably in the detection of colorectal cancer.
Specimen Collected from Subject As a sample obtained from a subject in the detection method of the present invention, specimens collected from a subject (i.e., samples isolated from a living body), more particularly, any body fluid collected (preferably blood), an excised specimen from the affected area of the subject, a biopsy sample or scraping specimen, feces, urine, a digestive tract lavage fluid, or the like, can be used. The digestive tract lavage fluid may be a lavage fluid of the whole digestive tract, or a lavage fluid of the digestive tract containing at least a site to be analyzed, for example, a lavage fluid of the lower digestive tract or a lavage fluid of the large intestine. In view of detection sensitivity, a sample containing cells from the site to be analyzed in the target organ is preferable, and an excised specimen or a biopsy sample from the site to be analyzed of the subject is more preferable.
Treatment of Specimen The detection method of the NTRK3 fusion gene or the NTRK3 fusion protein of the present invention can be carried out by preparing a tissue section, a cell suspension, or the like of the sample obtained from the subject, and detecting the NTRK3 fusion gene or the NTRK3 fusion protein in the cells contained in the tissue section or the cell suspension by a technique well-known to those skilled in the art. Alternatively, a lysate is prepared from the sample obtained from the subject, and the genes or proteins contained in the lysate are extracted, and the NTRK3 fusion gene or the NTRK3 fusion protein can be detected in the obtained extract by a technique well-known to those skilled in the art. In connection with this, the detection of the NTRK3 fusion gene may be a detection of genomic DNA of the NTRK3 fusion gene; a detection of mRNA, which is a transcript of the genomic DNA; or a detection of cDNA obtained from the mRNA as a template.

The detection method of the ETV6 fusion gene or the ETV6 fusion protein of the present invention can be carried out by preparing a tissue section, a cell suspension, or the like of the sample obtained from the subject, and detecting the ETV6 fusion gene or the ETV6 fusion protein in the cells contained in the tissue section or the cell suspension by a technique well-known to those skilled in the art. Alternatively, a lysate is prepared from the sample obtained from the subject, and the genes or proteins contained in the lysate are extracted, and the ETV6 fusion gene or the ETV6 fusion protein can be detected in the obtained extract by a technique well-known to those skilled in the art. In connection with this, the detection of the ETV6 fusion gene may be a detection of genomic DNA of the ETV6 fusion gene; a detection of mRNA, which is a transcript of the genomic DNA; or a detection of cDNA obtained from the mRNA as a template.
Target to be Detected in the Detection Method of the Present Invention The detection method of the present invention includes a method for detecting an NTRK3 fusion in a sample obtained from a subject, namely, a method for detecting a fusion protein containing the NTRK3 kinase region (also called "NTRK3 fusion protein"), and a method for detecting a fusion gene encoding the fusion protein (also called "NTRK3 fusion gene").

The detection method of the present invention includes a method for detecting an ETV6 fusion in a sample obtained from a subject, namely, a method for detecting an ETV6 fusion protein, and a method for detecting a fusion gene encoding the fusion protein (also called "ETV6 fusion gene").
NTRK3 Fusion: NTRK3 Fusion Protein and NTRK3 Fusion Gene The term "NTRK3 fusion" as used herein includes the NTRK3 fusion protein and the NTRK3 fusion gene.

The NTRK3 fusion gene in the present invention is a polynucleotide encoding the NTRK3 fusion protein.

The NTRK3 fusion protein in the present invention is a fusion protein constructed from a polypeptide derived from the NTRK3 protein, and a polypeptide derived from a protein other than NTRK3. The polypeptide derived from the NTRK3 protein is not particularly limited, so long as it comprises at least a polypeptide of the NTRK3 kinase region in the NTRK3 protein. The polypeptide derived from the protein other than NTRK3 is not particularly limited, so long as it comprises at least a portion of the other protein.

The other protein is not particularly limited, so long as the NTRK3 fusion protein, which is constructed by fusing the other protein to a portion of the NTRK3 protein containing the NTRK3 kinase domain, has oncogenic potential. It is preferable that the constructed NTRK3 fusion protein has oncogenic potential by constitutively maintaining the NTRK3 kinase activation in the NTRK3 fusion protein.

The NTRK3 fusion protein may comprise the third polypeptide, which is neither the polypeptide derived from the NTRK3 protein, nor the polypeptide derived from a protein other than the NTRK3 protein, so long as the NTRK3 kinase activation is constitutively maintained, and the constructed NTRK3 fusion protein has oncogenic potential. The third polypeptide may be located at the N-terminus of the NTRK3 fusion protein, at the C-terminus of the NTRK3 fusion protein, or between the polypeptide derived from the NTRK3 protein and the polypeptide derived from a protein other than the NTRK3 protein.

As the NTRK3 fusion protein, a fusion protein in which the other protein is the ETV6 protein is most preferable. More particularly, a fusion protein of the NTRK3 protein and the ETV6 protein (hereinafter also referred to as an ETV6-NTRK3 fusion protein), constructed from an NTRK3-derived polypeptide comprising at least a polypeptide of the NTRK3 kinase region, and an ETV6-derived polypeptide comprising a polypeptide of at least a portion of the ETV6 protein, is preferable.

ETV6 Fusion: ETV6 Fusion Protein and ETV6 Fusion Gene

The term "ETV6 fusion" as used herein includes the ETV6 fusion protein and the ETV6 fusion gene.

The ETV6 fusion gene in the present invention is a polynucleotide encoding the ETV6 fusion protein.

The ETV6 fusion protein in the present invention is a fusion protein constructed from a polypeptide derived from the ETV6 protein, and a polypeptide derived from a protein other than the ETV6 protein. The polypeptide derived from the ETV6 protein is not particularly limited, so long as it comprises at least a polypeptide of the ETV6 protein. The polypeptide derived from the protein other than ETV6 is not particularly limited, so long as it comprises at least a portion of the other protein.

The other protein is not particularly limited, so long as the ETV6 fusion protein, which is constructed by fusing the other protein to a portion of the ETV6 protein, has oncogenic potential. It is preferable that the ETV6 fusion protein has oncogenic potential by constitutively maintaining the activation of a functional domain (preferably a kinase domain) of the other protein.

The ETV6 fusion protein may comprise the third polypeptide, which is neither the polypeptide derived from the ETV6 protein, nor the polypeptide derived from a protein other than the ETV6 protein, so long as the activation of the functional domain of the protein other than the ETV6 protein is constitutively maintained by fusing it to a portion of the ETV6 protein, and the constructed ETV6 fusion protein has oncogenic potential. The third polypeptide may be located at the N-terminus of the ETV6 fusion protein, at the C-terminus of the ETV6 fusion protein, or between the polypeptide derived from the ETV6 protein and the polypeptide derived from the protein other than the ETV6 protein.

As the ETV6 fusion protein, a fusion protein in which the other protein is the NTRK3 protein is most preferable. More particularly, a fusion protein of the ETV6 protein and the NTRK3 protein (hereinafter also referred to as an ETV6-NTRK3 fusion protein), constructed from an ETV6-derived polypeptide comprising a polypeptide of at least a portion of the ETV6 protein, and a polypeptide of at least a portion of the NTRK3 protein comprising a polypeptide of at least the NTRK3 kinase region, is preferable.

As the "ETV6-NTRK3 fusion protein", the following polypeptides (a) to (d) are most preferable:

(a) a polypeptide consisting of the amino acid sequence of SEQ ID NO: 2, (b) a polypeptide with oncogenic potential comprising the amino acid sequence of SEQ ID NO: 2, (c) a polypeptide with oncogenic potential comprising an amino acid sequence that has at least 80% identity to the amino acid sequence of SEQ ID NO: 2 (hereinafter referred to as a "homologous polypeptide"), and (d) a polypeptide with oncogenic potential comprising an amino acid sequence in which one or several amino acids are deleted, substituted, and/or inserted in the amino acid sequence of SEQ ID NO: 2 (hereinafter referred to as a "variation functionally equivalent").

The amino acid sequence of SEQ ID NO: 2 is a sequence encoded by the nucleotide sequence of SEQ ID NO: 1. The nucleotide sequence of SEQ ID NO: 1 consists of a nucleotide sequence from the initiation codon ATG to exon 5 of the ETV6 gene and a nucleotide sequence from exon 15 to the stop codon in exon 19 of the NTRK3 gene. In the nucleotide sequence of SEQ ID NO: 1, the sequence of nucleotides 1-1009 is derived from the ETV6 gene, and the sequence of nucleotides 1010-1653 is derived from the NTRK3 gene. Hereinafter the polynucleotide consisting of the nucleotide sequence of SEQ ID NO: 1 is referred to as "ETV6ex5-NTRK3ex15".

The number of amino acids capable of being deleted, substituted, and/or inserted in the "variation functionally equivalent" is 1 to several amino acids, preferably 1 to 10, more preferably 1 to 7, and most preferably 1 to 5.

The "homologous polypeptide" is a "polypeptide with oncogenic potential comprising an amino acid sequence that has at least 80% identity to the amino acid sequence of SEQ ID NO: 2". With respect to the identity, a polypeptide comprising an amino acid sequence that has, preferably at least 90% identity, more preferably at least 95% identity, and still more preferably at least 98% identity, is preferable.

The term "identity" as used herein means the value "Identity" obtained by a NEEDLE program (J Mol Biol 1970; 48: 443-453) search, using the following default parameters:

Gap penalty=10
Extend penalty=0.5
Matrix=EBLOSUM62

Embodiments of Detection Method of the Present Invention (Method for Detecting Fusion Gene and Fusion Protein)

The detection method of the present invention includes: a detection method comprising a step of detecting the cleavage of the NTRK3 gene, or the cleavage of a polypeptide encoded by the NTRK3 gene, in a sample derived from the digestive system obtained from a subject; and a detection method comprising a step of detecting the presence of a fusion gene constructed from the NTRK3 gene and a gene other than the NTRK3 gene, or the presence of a fusion protein encoded by the fusion gene, in a digestive system-derived sample obtained from a subject.

The detection method of the present invention includes: a detection method comprising a step of detecting the cleavage of the ETV6 gene, or the cleavage of a polypeptide encoded by the ETV6 gene, in a sample derived from the digestive system obtained from a subject; and a detection method comprising a step of detecting the presence of a fusion gene constructed from the ETV6 gene and a gene other than the ETV6 gene, or the presence of a fusion protein encoded by the fusion gene, in a digestive system-derived sample obtained from a subject.

Embodiments of Detecting NTRK3 Fusion Gene

Hereinafter, embodiments of detecting the NTRK3 fusion gene will be explained, but the present invention is not limited to these embodiments.

In connection with this, the detection of the specific region of the gene in each of the following embodiments may be carried out, regardless of the examples, using a probe or primers designed based on the pre-analyzed nucleotide sequence, or by sequencing.

Embodiments of Detecting NTRK3 Fusion Gene (1)

Embodiment of Detecting NTRK3 Fusion Gene (1-a)

As an embodiment of detecting the NTRK3 fusion gene, on the basis of the fact that, when the NTRK3 fusion gene is constructed, the NTRK3 gene is cleaved into two or more polynucleotides, the NTRK3 fusion gene can be detected by detecting a state in which the NTRK3 gene is cleaved, namely, a state in which the continuity of the 5' terminal region of the NTRK3 gene and the 3' terminal region of the NTRK3 gene is lost.

More particularly, the NTRK3 fusion gene can be detected, for example, using the first probe that specifically hybridizes to the 5' terminal region of the NTRK3 gene, and the second probe that specifically hybridizes to the 3' terminal region of the NTRK3 gene, by detecting the fact that the two gene regions are apart from each other on a chromosome.

In connection with this, the NTRK3 fusion gene may be detected by confirming a state in which the other gene, which constitutes the fusion gene by fusing it to a polynucleotide derived from the NTRK3 gene, is cleaved, using the above-mentioned method.

Embodiment of Detecting NTRK3 Fusion Gene (1-b)

As another embodiment, the NTRK3 fusion gene can be detected by separately and specifically detecting the expression levels of the 5' terminal region and the 3' terminal region of the NTRK3 gene, and calculating the ratio of the expression levels. More particularly, for example, when the expression level of the 5' terminal region of the NTRK3 gene is different from the expression level of the 3' terminal region of the NTRK3 gene, the NTRK3 fusion gene can be detected.

Alternatively, the NTRK3 fusion gene may be detected by confirming the other gene (i.e., the gene other than the NTRK3 gene), which constitutes the NTRK3 fusion gene together with the NTRK3 gene, using the above-mentioned method.

Embodiment of Detecting NTRK3 Fusion Gene (1-c)

As still another embodiment, in the case where the forming process of the NTRK3 fusion gene is accompanied by a duplication of at least a portion of the NTRK3 or the other gene, namely, in the case where the NTRK3 fusion gene is constructed from a duplicated polynucleotide derived from the NTRK3 gene, and a duplicated polynucleotide derived from the other gene (i.e., the gene other than the NTRK3 gene), which constitutes the NTRK3 fusion gene together with the NTRK3, the NTRK3 fusion gene can be detected by detecting the duplication of the polynucleotide derived from the NTRK3 gene, or the polynucleotide derived from the other gene.

Embodiment of Detecting NTRK3 Fusion Gene (2)

As an embodiment of detecting the NTRK3 fusion gene, on the basis of the fact that the NTRK3 fusion gene is constructed by fusing a polynucleotide derived from the NTRK3 gene to a polynucleotide derived from the gene other than the NTRK3, the NTRK3 fusion gene can be detected by detecting a fusion polynucleotide sequentially containing at least a portion of the polynucleotide derived from the NTRK3 gene, and at least a portion of the polynucleotide derived from the gene other than the NTRK3, in the NTRK3 fusion gene.

More particularly, the NTRK3 fusion gene can be detected, for example, using the first probe that specifically hybridizes to the 5' terminal region of a polynucleotide derived from the gene other than the NTRK3, and the second probe that specifically hybridizes to the 3' terminal region of the NTRK3 gene, by detecting the fact that the two gene regions are adjacent to each other on a chromosome. When the gene other than the NTRK3 is ETV6, namely, when the NTRK3 fusion gene is the ETV6-NTRK3 fusion gene, a probe specifically hybridizing to the 5' terminal region of a polynucleotide derived from the ETV6 gene may be used, as the first probe.

Embodiment of Detecting NTRK3 Fusion Gene (3)

As an embodiment of detecting the NTRK3 fusion gene, on the basis of the fact that the NTRK3 fusion gene is constructed by fusing a polynucleotide derived from the NTRK3 gene to a polynucleotide derived from the gene other than the NTRK3 at the fusion point, the NTRK3 fusion gene can be detected by detecting a fusion polynucleotide containing the fusion point and sequentially containing at least a portion of the polynucleotide derived from the NTRK3 gene, and at least a portion of the polynucleotide derived from the gene other than the NTRK3, in the NTRK3 fusion gene.

More particularly, the NTRK3 fusion gene can be detected by carrying out a PCR reaction, for example, using the first primer that specifically anneals to the 5' terminal region of a polynucleotide derived from the gene other than the NTRK3 gene, and the second primer that specifically anneals to the 3' terminal region of the NTRK3 gene, and confirming the fact that a desired PCR product showing the presence of the fusion point can be obtained.

Embodiments of Detecting NTRK3 Fusion Protein

Hereinafter, embodiments of detecting the NTRK3 fusion protein will be explained, but the present invention is not limited to these embodiments.

Embodiments of Detecting NTRK3 Fusion Protein (1)

Embodiment of Detecting NTRK3 Fusion Protein (1-a)

As an embodiment of detecting the NTRK3 fusion protein, on the basis of the fact that, when the NTRK3 fusion gene is constructed, the NTRK3 protein encoded by the NTRK3 gene is also cleaved, the NTRK3 fusion protein can be detected by detecting a state in which the NTRK3 protein is cleaved, namely, a state in which the N-terminal region and the C-terminal region of the NTRK3 protein are not continuous, and are cleaved.

More particularly, the NTRK3 fusion protein can be detected, for example, using the first antibody that specifically binds to the N-terminal region of the NTRK3 protein, and the second antibody that specifically binds to the C-terminal region of the NTRK3 protein, by confirming the fact that the two regions are not present in the same protein (namely, the two regions are present in different proteins).

Alternatively, the NTRK3 fusion protein may be detected by confirming the other protein, which constitutes the NTRK3 fusion protein together with the NTRK3 protein, using the above-mentioned method.

Embodiment of Detecting NTRK3 Fusion Protein (1-b)

As another embodiment, the NTRK3 fusion protein can be detected by separately and specifically detecting the expression levels of the N-terminal region and the C-terminal region of the NTRK3 protein, and calculating the ratio of the expression levels. More particularly, the NTRK3 fusion protein can be detected, for example, using the fact that the expression level of the N-terminal region of the NTRK3 protein is different from the expression level of the C-terminal region of the NTRK3 protein, as an index.

Alternatively, the NTRK3 fusion protein may be detected by confirming the other protein, which constitutes the NTRK3 fusion protein together with the NTRK3 protein, using the above-mentioned method.

Embodiment of detecting NTRK3 fusion protein (2) As an embodiment of detecting the NTRK3 fusion protein, on the basis of the fact that the NTRK3 fusion protein is constructed by fusing a polypeptide derived from the NTRK3 protein to a polypeptide derived from the protein other than the NTRK3, the NTRK3 fusion protein can be detected by detecting a fusion polypeptide sequentially containing at least a portion of the polypeptide derived from the NTRK3 protein, and at least a portion of the polypeptide derived from the protein other than the NTRK3, in the NTRK3 fusion protein.

More particularly, the NTRK3 fusion protein can be detected, for example, using the first antibody that specifically binds to the N-terminal region of the protein other than the NTRK3 protein, and the second antibody that specifically binds to the C-terminal region of the NTRK3 protein, by confirming the fact that the two regions are present in the same protein.

Embodiment of Detecting NTRK3 Fusion Protein (3)

As an embodiment of detecting the NTRK3 fusion protein, on the basis of the fact that the NTRK3 fusion protein is constructed by fusing a polypeptide derived from the NTRK3 protein to a polypeptide derived from the protein other than the NTRK3 at the fusion point, the NTRK3 fusion protein can be detected by detecting a fusion polypeptide containing the fusion point and sequentially containing at least a portion of the polypeptide derived from the NTRK3 protein, and at least a portion of the polypeptide derived from the protein other than the NTRK3, in the NTRK3 fusion protein.

More particularly, the NTRK3 fusion protein can be detected, for example, by an immunoassay using an antibody that specifically recognizes a polypeptide containing the fusion point of the NTRK3 fusion protein.

Embodiment of Detecting NTRK3 Fusion Protein (4)

As an embodiment of detecting the NTRK3 fusion protein, the NTRK3 fusion protein can be detected using the activity of the NTRK3 fusion protein, as an index.

More particularly, the NTRK3 fusion protein can be detected, for example, by measuring a kinase activity of the NTRK3 protein, under the conditions that the activity of the wild-type NTRK3 protein is inhibited using an inhibitor for the wild-type NTRK3 protein, and using, as an index, the fact that the activity is higher, in comparison with the case where the NTRK3 fusion protein is not contained (namely, the wild-type NTRK3 protein is contained alone). In connection with this, the measurement method for the kinase activity of the NTRK3 protein may be appropriately selected from well-known methods for those skilled in the art. For example, the phosphorylation state of a molecule to be phosphorylated by the NTRK3 may be detected.

The detection of the NTRK3 fusion protein may be carried out using, as an index, the presence of the full-length polypeptide that constitutes the NTRK3 fusion protein, or the presence of a polypeptide that constitutes part of the NTRK3 fusion protein, and it is not particularly limited, so long as the presence of the NTRK3 fusion protein can be confirmed.

Embodiments of Detecting ETV6 Fusion Gene

Hereinafter, embodiments of detection of the ETV6 fusion gene will be explained, but the present invention is not limited to these embodiments.

In connection with this, the detection of the specific region of the gene in each of the following embodiments may be carried out, regardless of the examples, using a probe or primers designed based on the pre-analyzed nucleotide sequence, or by sequencing.

Embodiments of Detecting ETV6 Fusion Gene (1)

Embodiment of Detecting ETV6 Fusion Gene (1-a)

As an embodiment of detecting the ETV6 fusion gene, on the basis of the fact that, when the ETV6 fusion gene is constructed, the ETV6 gene is cleaved into two or more polynucleotides, the ETV6 fusion gene can be detected by detecting a state in which the ETV6 gene is cleaved, namely, a state in which the continuity of the 5' terminal region of the ETV6 gene and the 3' terminal region of the ETV6 gene is lost.

More particularly, the ETV6 fusion gene can be detected, for example, using the first probe that specifically hybridizes to the 5' terminal region of the ETV6 gene, and the second probe that specifically hybridizes to the 3' terminal region of the ETV6 gene, by detecting the fact that the two gene regions are apart from each other on a chromosome.

In connection with this, the ETV6 fusion gene may be detected by confirming a state in which the other gene, which constitutes the fusion gene by fusing it to a polynucleotide derived from the ETV6 gene, is cleaved, using the above-mentioned method.

Embodiment of Detecting ETV6 Fusion Gene (1-b)

As another embodiment, the ETV6 fusion gene can be detected by separately and specifically detecting the expression levels of the 5' terminal region and the 3' terminal region of the ETV6 gene, and calculating the ratio of the expression levels. More particularly, for example, when the expression level of the 5' terminal region of the ETV6 gene is different from the expression level of the 3' terminal region of the ETV6 gene, the ETV6 fusion gene can be detected.

Alternatively, the ETV6 fusion gene may be detected by confirming the other gene, which constitutes the ETV6 fusion gene together with the ETV6 gene, using the above-mentioned method.

Embodiment of Detecting ETV6 Fusion Gene (1-c)

As still another embodiment, in the case where the forming process of the ETV6 fusion gene is accompanied by a duplication of at least a portion of the ETV6 gene or the other gene, namely, in the case where the ETV6 fusion gene is constructed from a duplicated polynucleotide derived from the ETV6 gene, and a duplicated polynucleotide derived from the other gene, which constitutes the ETV6 fusion gene together with the ETV6, the ETV6 fusion gene can be detected by detecting the duplication of the polynucleotide derived from the ETV6 gene, or the polynucleotide derived from the other gene.

Embodiment of Detecting ETV6 Fusion Gene (2)

As an embodiment of detecting the ETV6 fusion gene, on the basis of the fact that the ETV6 fusion gene is constructed by fusing a polynucleotide derived from the ETV6 gene to a polynucleotide derived from the gene other than the ETV6, the ETV6 fusion gene can be detected by detecting a fusion polynucleotide sequentially containing at least a portion of the polynucleotide derived from the ETV6 gene, and at least a portion of the polynucleotide derived from the gene other than the ETV6, in the ETV6 fusion gene.

More particularly, the ETV6 fusion gene can be detected, for example, using the first probe that specifically hybridizes to the 5' terminal region of a polynucleotide derived from the ETV6 gene, and the second probe that specifically hybridizes to the 3' terminal region of the gene other than the ETV6 gene, by detecting the fact that the two gene regions are adjacent to each other on a chromosome. When the gene other than the ETV6 is NTRK3, namely, when the ETV6 fusion gene is the ETV6-NTRK3 fusion gene, a probe specifically hybridizes to the 3' terminal region of a polynucleotide derived from the NTRK3 gene may be used, as the second probe.

Embodiment of Detecting ETV6 Fusion Gene (3)

As an embodiment of detecting the ETV6 fusion gene, on the basis of the fact that the ETV6 fusion gene is constructed by fusing a polynucleotide derived from the ETV6 gene to a polynucleotide derived from the gene other than the ETV6 at the fusion point, the ETV6 fusion gene can be detected by detecting a fusion polynucleotide containing the fusion point and sequentially containing at least a portion of the polynucleotide derived from the ETV6 gene, and at least a portion of the polynucleotide derived from the gene other than the ETV6, in the ETV6 fusion gene.

More particularly, the ETV6 fusion gene can be detected by carrying out a PCR reaction, for example, using the first primer that specifically anneals to the 5' terminal region of a polynucleotide derived from the ETV6 gene, and the second primer that specifically anneals to the 3' terminal region of the gene other than the ETV6 gene, and confirming the fact that a desired PCR product showing the presence of the fusion point can be obtained.

Embodiments of Detecting ETV6 Fusion Protein

Hereinafter, embodiments of detection of the ETV6 fusion protein will be explained, but the present invention is not limited to these embodiments.

Embodiments of Detecting ETV6 Fusion Protein (1)

Embodiment of Detecting ETV6 Fusion Protein (1-a)

As an embodiment of detecting the ETV6 fusion protein, on the basis of the fact that, when the ETV6 fusion gene is constructed, the ETV6 protein encoded by the ETV6 gene is also cleaved, the ETV6 fusion protein can be detected by detecting a state in which the ETV6 protein is cleaved, namely, a state in which the continuity between the N-terminal region and the C-terminal region of the ETV6 protein is lost.

More particularly, the ETV6 fusion protein can be detected, for example, using the first antibody that specifically binds to the N-terminal region of the ETV6 protein, and the second antibody that specifically binds to the C-terminal region of the ETV6 protein, by confirming the fact that the two regions are not present in the same protein.

Alternatively, the ETV6 fusion protein may be detected by confirming the other protein, which constitutes the ETV6 fusion protein together with the ETV6 protein, using the above-mentioned method.

Embodiment of Detecting ETV6 Fusion Protein (1-b)

As another embodiment, the ETV6 fusion protein can be detected by separately and specifically detecting the expression levels of the N-terminal region and the C-terminal region of the ETV6 protein, and calculating the ratio of the expression levels. More particularly, the ETV6 fusion protein can be detected, for example, using the fact that the expression level of the N-terminal region of the ETV6 protein is different from the expression level of the C-terminal region of the ETV6 protein, as an index.

Alternatively, the ETV6 fusion protein may be detected by confirming the other protein, which constitutes the ETV6 fusion protein together with the ETV6 protein, using the above-mentioned method.

Embodiment of Detecting ETV6 Fusion Protein (2)

As an embodiment of detecting the ETV6 fusion protein, on the basis of the fact that the ETV6 fusion protein is constructed by fusing a polypeptide derived from the ETV6 protein to a polypeptide derived from the protein other than the ETV6, the ETV6 fusion protein can be detected by detecting a fusion polypeptide sequentially containing at least a portion of the polypeptide derived from the ETV6 protein, and at least a portion of the polypeptide derived from the protein other than the ETV6, in the ETV6 fusion protein.

More particularly, the ETV6 fusion protein can be detected, for example, using the first antibody that specifically binds to the N-terminal region of the ETV6 protein, and the second antibody that specifically binds to the C-terminal region of the protein other than the ETV6 protein, by confirming the fact that the two regions are present in the same protein.

Embodiment of Detecting ETV6 Fusion Protein (3)

As an embodiment of detecting the NTRK3 fusion protein, on the basis of the fact that the ETV6 fusion protein is constructed by fusing a polypeptide derived from the ETV6 protein to a polypeptide derived from the protein other than the ETV6 protein at the fusion point, the ETV6 fusion protein can be detected by detecting a fusion polypeptide containing the fusion point and sequentially containing at least a portion of the polypeptide derived from the ETV6 protein, and at least a portion of the polypeptide derived from the protein other than the ETV6, in the ETV6 fusion protein.

More particularly, the ETV6 fusion protein can be detected, for example, by an immunoassay using an antibody that specifically recognizes a polypeptide containing the fusion point of the ETV6 fusion protein.

Embodiment of Detecting ETV6 Fusion Protein (4)

As an embodiment of detecting the ETV6 fusion protein, the ETV6 fusion protein can be detected using the activity of the ETV6 fusion protein, as an index.

More particularly, for example, when the other protein, which constitutes the fusion protein together with the ETV6 protein, is a protein having an enzyme activity, the ETV6 fusion protein can be detected by using, as an index, the fact that the activity is higher, in comparison with the case where the ETV6 fusion protein is not contained (namely, the wild-type ETV6 protein is contained alone). In connection with this, the measurement method for the enzyme activity may be appropriately selected from well-known methods for those skilled in the art. For example, when the other protein is a protein having a kinase activity (preferably the NTRK3 protein), the phosphorylation state of a molecule to be phosphorylated by the ETV6 fusion protein may be detected.

The detection of the ETV6 fusion protein may be carried out using, as an index, the presence of the full-length polypeptide that constitutes the ETV6 fusion protein, or the presence of a polypeptide that constitutes part of the ETV6 fusion protein, and it is not particularly limited, so long as the presence of the ETV6 fusion protein can be confirmed.

Techniques Used in Detection Method

Hereinafter, the steps and detection techniques of the detection of the NTRK3 fusion gene (genomic DNA, mRNA, or cDNA), the detection of the ETV6 fusion gene (genomic DNA, mRNA, or cDNA), the detection of the NTRK3 fusion protein, and the detection of the ETV6 fusion protein will be further explained in detail, but the present invention is not limited thereto.

In the case where a gene (genomic DNA or mRNA) or a protein is extracted from the sample obtained from a subject, or in the case where tissue sections, a cell suspension, or the like is prepared, those skilled in the art can appropriately select preferred techniques for detecting the NTRK3 fusion gene or the ETV6 fusion gene, or the NTRK3 fusion protein or the ETV6 fusion protein in the prepared sample.

Detection of Fusion Gene

The detection of the NTRK3 fusion gene or the ETV6 fusion gene may be a detection of genomic DNA of the NTRK3 fusion gene or the ETV6 fusion gene, a detection of an mRNA that is a transcriptional product from the genomic DNA, or a detection of a cDNA obtained by using the mRNA as a template.

As a technique for detecting the NTRK3 fusion gene (genomic DNA or mRNA) or the ETV6 fusion gene (genomic DNA or mRNA) in the sample obtained from a subject, any technique, well-known by those skilled in the art, used in the detection of a gene, for example, a hybridization technique using a probe (a nucleic acid probe or the like) which hybridizes to at least a portion of the NTRK3 fusion gene or the ETV6 fusion gene, a gene amplification technique using primers which anneal to at least a portion of the NTRK3 fusion gene or the ETV6 fusion gene, or the like, and a technique obtained by modifying these techniques, can be used.

More particularly, any technique, for example, PCR, LCR (Ligase chain reaction), SDA (Strand displacement amplification), NASBA (Nucleic acid sequence-based amplification), ICAN (Isothermal and chimeric primer-initiated amplification of nucleic acids), an LAMP (Loop-mediated isothermal amplification) method, a TMA method (Gen-Probe's TMA system), an in situ hybridization method, a microarray method, Northern hybridization, Southern hybridization, a dot blot method, an RNA protection method, DNA sequencing, RNA sequencing, or the like, can be used.

Detection of Genomic DNA

The in situ hybridization technique may be preferably used in the detection of genomic DNA. The detection utilizing the in situ hybridization technique may be carried out, for example, in accordance with a known FISH method, or by a fusion assay, which is a combination of a chromogenic in situ hybridization (CISH) method and a silver in situ hybridization (SISH) method. Preferably, it can be detected by a FISH method, split assay; or a FISH method, fusion assay, as described in Examples 4 and 5.

Alternatively, the DNA sequencing technique can be preferably used in the detection of genomic DNA. For the sequencing, a sequencer based on a conventional Sanger method may be used, but it is preferable to use a next-generation sequencer in view of the efficiency of the analysis (for example, see Metzker M L, Nat Rev Genet. 2010 January; 11(1): 31-46). As the next-generation sequencer, MiSeq/HiSeq (Illumina), SOLiD System (Life Technologies), 454 Sequence System (GS FLX+/GS Junior) (Roche), or the like, may be exemplified. In the sequencing, the efficiency of analysis can be improved by enriching the regions where the fusion gene might be present, using a sequence capture technique, or the like. As the sequence capture technique, Roche NimbleGen (Roche), Sure Select (Agilent Technologies), or the like, may be exemplified.

Hereinafter, typical methods for detecting genomic DNA will be exemplified, but the present invention is not limited to these methods.

FISH Method, Split Assay

In the FISH method, split assay for the NTRK3 fusion gene, a combination of a polynucleotide that covers the 5' terminal genomic region of the NTRK3 gene and is fluorescent-labeled, and another polynucleotide that covers the 3' terminal genomic region of the NTRK3 gene and is fluorescent-labeled with a different fluorescent dye is used as the probe for detection, as explained in detail in Example 5 below. In the normal case, since two gene regions (the 5' terminal region and the 3' terminal region of each gene) are adjacent to each other, two signals are detected as an overlapped color (for example, when a red fluorescent dye and a green fluorescent dye are used, yellow). On the other hand, in the case where two gene regions are cleaved due to translocation or inversion, two signals (for example, red and green) derived from the fluorescent dyes are detected separately and apart from each other. Therefore, in the FISH method, split assay, the presence of the NTRK3 fusion gene is detected by detecting the fact that the 5' terminal genomic region of the NTRK3 gene and the 3' terminal genomic region of the NTRK3 gene are apart from each other on a chromosome.

In the FISH method, split assay for the ETV6 fusion gene, a combination of a polynucleotide that covers the 5' terminal genomic region of the ETV6 gene and is fluorescent-labeled, and another polynucleotide that covers the 3' terminal genomic region of the ETV6 gene and is fluorescent-labeled with a different fluorescent dye is used as the probe for detection, as explained in detail in Example 5 below. In the normal case, since two gene regions (the 5' terminal region and the 3' terminal region of each gene) are adjacent to each other, two signals are detected as an overlapped color (for example, when a red fluorescent dye and a green fluorescent dye are used, yellow). On the other hand, in the case where two gene regions are cleaved due to translocation or inversion, two signals (for example, red and green) derived from the fluorescent dyes are detected separately and apart from each other. Therefore, in the FISH method, split assay, the presence of the ETV6 fusion gene is detected by detecting the fact that the 5' terminal genomic region of the ETV6 gene and the 3' terminal genomic region of the ETV6 gene are apart from each other on a chromosome.

In the case where the NTRK3 fusion gene is the ETV6-NTRK3 fusion gene, the ETV6-NTRK3 fusion gene can be detected by using, as the probe for detection, a combination of a polynucleotide that covers the 5' terminal genomic region of the ETV6 gene and is fluorescent-labeled, and another polynucleotide that covers the 3' terminal genomic region of the ETV6 gene and is fluorescent-labeled with a different fluorescent dye, or a combination of a polynucleotide that covers the 5' terminal genomic region of the ETV6 gene and is fluorescent-labeled, and another polynucleotide that covers the 3' terminal genomic region of the ETV6 gene and is fluorescent-labeled with a different fluorescent dye, as shown in Example 5 below.

FISH Method, Fusion Assay

In the FISH method, fusion assay, for example, in the case where the NTRK3 fusion gene is the ETV6-NTRK3 fusion gene, a combination of a polynucleotide that covers the 5' terminal genomic region of the ETV6 gene and is fluorescent-labeled, and another polynucleotide that covers the 3' terminal genomic region of the NTRK3 gene and is fluorescent-labeled with a different fluorescent dye can be used as the probe for detection, as explained in detail in Example 4 below. In the normal case, two signals (for example, red and green) derived from the fluorescent dyes are detected separately and apart from each other. On the other hand, in the case where two gene regions are adjacent to each other due to translocation or inversion, two signals are detected as an overlapped color (for example, yellow).

Detection of Gene Duplication Using FISH Method

With respect to a gene duplication associated with the construction of the NTRK3 fusion gene, for example, in the case where the NTRK3 fusion gene is the ETV6-NTRK3 fusion gene, a polynucleotide that covers at least a portion of the 3' terminal genomic region of the NTRK3 gene and fluorescent-labeled can be used as the probe for detection. The NTRK3 fusion gene can be detected by detecting the fact that a strong signal (for example, two times or more) is obtained, in comparison with the case of the wild-type NTRK3 gene alone.

In connection with this, the NTRK3 fusion gene may be detected by this method, using a probe for detecting the 5' genomic region of another gene that constitutes the fusion gene by fusing it to a polynucleotide derived from the NTRK3 gene (for example, when the NTRK3 fusion gene is the ETV6-NTRK3 fusion gene, another gene is the ETV6 gene).

With respect to a gene duplication associated with the construction of the ETV6 fusion gene, for example, in the case where the ETV6 fusion gene is the ETV6-NTRK3 fusion gene, a polynucleotide that covers at least a portion of the 5' terminal genomic region of the ETV6 gene and is fluorescent-labeled, can be used as the probe for detection. The ETV6 fusion gene can be detected by detecting the fact that a strong signal (for example, two times or more) is obtained, in comparison with the case of the wild-type ETV6 gene alone.

In connection with this, the ETV6 fusion gene may be detected by this method, using a probe for detecting the 3' genomic region of another gene that constitutes the fusion gene by fusing it to a polynucleotide derived from the ETV6 gene (for example, when the ETV6 fusion gene is the ETV6-NTRK3 fusion gene, another gene is the NTRK3 gene).

Detection of Gene Duplication Using CGH Array Analysis

The gene duplication associated with the construction of the NTRK3 fusion gene or the construction of the ETV6 fusion gene can be detected by a comparative genomic hybridization (CGH) array analysis (for example, Agilent CGH/CNV Array Analysis; Agilent Technologies).

Detection of Gene Duplication Using Next-Generation Sequencer

The gene duplication associated with the construction of the NTRK3 fusion gene or the construction of the ETV6 fusion gene can be detected by a next-generation sequencer. More particularly, the NTRK3 fusion gene or the ETV6 fusion gene can be detected by detecting the fact that the coverage of the gene duplication portion is high (the redundancy of the portion is high at the time of the annotation, using the sequence of a DNA fragment to be analyzed, as the reference sequence) in the analysis using a next-generation sequencer.

Probe to be Used in Detection (for Genome)

As the probe used in hybridization to detect the NTRK3 fusion gene, a probe that hybridizes to a polynucleotide of at least a portion of the NTRK3 fusion gene, or a complementary strand thereof, under stringent conditions (preferably, under more stringent conditions), is preferable.

For example, in the case where genomic DNA of the NTRK3 fusion gene containing the fusion point is detected, a probe comprising a nucleic acid molecule consisting of at least 32 consecutive nucleotides containing 16 nucleotides at the upstream and 16 nucleotides at the downstream, by which the fusion point of the NTRK3 fusion gene is sandwiched (more particularly, nucleotides 994-1025 of SEQ ID NO: 1), or a complementary strand thereof, may be used.

As the probe used in hybridization to detect the ETV6 fusion gene, a probe that hybridizes to a polynucleotide of at least a portion of the ETV6 fusion gene, or a complementary strand thereof, under stringent conditions (preferably, under more stringent conditions), is preferable.

For example, in the case where genomic DNA of the ETV6 fusion gene containing the fusion point is detected, a probe comprising a nucleic acid molecule consisting of at least 32 consecutive nucleotides containing 16 nucleotides at the upstream and 16 nucleotides at the downstream, by which the fusion point of the ETV6 fusion gene is sandwiched (more particularly, nucleotides 994-1025 of SEQ ID NO: 1), or a complementary strand thereof, may be used.

For example, in the case where the NTRK3 fusion gene or the ETV6 fusion gene is the ETV6-NTRK3 fusion gene, as the probe that can be used in the FISH method, fusion assay, a combination of the first probe that specifically recognizes the 5' terminal genomic region of either of the ETV6 gene or the NTRK3 gene, and the second probe that specifically recognizes the 3' terminal genomic region of the other (preferably, a combination of the first probe that specifically recognizes the 5' terminal genomic region of the ETV6 gene, and the second probe that specifically recognizes the 3' terminal genomic region of the NTRK3 gene) can be used, more particularly, each combination of BAC clones used in Example 4 below may be exemplified.

On the other hand, for example, in the case where the NTRK3 fusion gene or the ETV6 fusion gene is the ETV6-NTRK3 fusion gene, as the probe that can be used in the FISH method, split assay, a combination of the first probe that specifically recognizes the 5' terminal genomic region of the NTRK3 gene, and the second probe that specifically recognizes the 3' terminal genomic region of the NTRK3 gene, or a combination of the first probe that specifically recognizes the 5' terminal genomic region of the ETV6 gene, and the second probe that specifically recognizes the 3' terminal genomic region of the ETV6 gene (preferably, a combination of the first probe that specifically recognizes the 5' terminal genomic region of the NTRK3 gene, and the second probe that specifically recognizes the 3' terminal genomic region of the NTRK3 gene) can be used, more particularly, each combination of BAC clones used in Example 5 below may be exemplified.

Detection of mRNA

Detection of mRNA can be carried out by analyzing the mRNA per se using a Northern hybridization method or the like, or by analyzing a complementary DNA (cDNA), which is synthesized by a well-known method for those skilled in the art, using the mRNA as a template.

The detection of RNA can be carried out, preferably using a sequence technique. In view of the efficiency of analysis, it is preferable to use a next-generation sequencer in the sequencing (for example, see Metzker M L, Nat Rev Genet. 2010 January; 11(1): 31-46). As the next-generation sequencer, MiSeq/HiSeq (Illumina), SOLiD System (Life Technologies), 454 Sequence System (GS FLX+/GS Junior) (Roche), or the like, may be exemplified. In the sequencing, the efficiency of analysis can be improved by enriching the regions where the fusion gene might be present, using a gene amplification reaction method as described below, a sequence capture technique, or the like. As the sequence capture technique, Roche NimbleGen (Roche), Sure Select (Agilent Technologies), or the like, may be exemplified.

Detection by Gene Amplification Reaction Method mRNA can be detected by a gene amplification method, using primers designed so as to specifically amplify a polynucleotide of at least a portion of the NTRK3 fusion gene, or the ETV6 fusion gene. Hereinafter typical methods for detecting mRNA will be exemplified, but the present invention is not limited to these methods.

PCR Method

For example, in the PCR method, a PCR product is analyzed by an agarose gel electrophoresis, and it can be confirmed whether or not an amplified fragment of the desired size can be obtained by an ethidium bromide staining or the like. When the amplified fragment of the desired size is obtained, it may be concluded that the NTRK3 fusion gene or the ETV6 fusion gene is present in a sample obtained from a subject. The NTRK3 fusion gene or the ETV6 fusion gene can be detected in this manner.

As the detection method of the NTRK3 fusion gene or the ETV6 fusion gene of the present invention, it is preferable that, in addition to the step of amplifying a specific polynucleotide by a gene amplification reaction in a sample obtained from a subject, it further comprises the step of detecting whether or not the amplified fragment of the desired size is obtained.

The PCR method is suitable to quantitatively detect the NTRK3 fusion gene or the ETV6 fusion gene.

Therefore, as previously described in Embodiment of detecting NTRK3 fusion protein (1-b), the PCR method is preferably used in the method of detecting the NTRK3 fusion gene by separately and specifically detecting the expression levels of the 5' terminal region and the 3' terminal region of the NTRK3 fusion gene, and calculating the ratio of the expression levels. Alternatively, the NTRK3 fusion gene can be detected by separately and specifically detecting the expression levels of the 5' terminal region and the 3' terminal region of the other gene (i.e., the gene other than the NTRK3 gene), which constitutes the NTRK3 fusion gene together with the NTRK3 gene, and calculating the ratio of the expression levels.

Further, as previously described in Embodiment of detecting ETV6 fusion protein (1-b), the PCR method is preferably used in the method of detecting the ETV6 fusion gene by separately and specifically detecting the expression levels of the 5' terminal region and the 3' terminal region of the ETV6 fusion gene, and calculating the ratio of the expression levels. Alternatively, the ETV6 fusion gene can be detected by separately and specifically detecting the expression levels of the 5' terminal region and the 3' terminal region of the other gene (i.e., the gene other than the ETV6 gene), which constitutes the ETV6 fusion gene together with the ETV6 gene, and calculating the ratio of the expression levels.

With respect to the PCR method, and the method of designing primers used in this method, the methods can be carried out by those skilled in the art in accordance with known methods.

For example, a sense primer and an antisense primer that are designed so as to specifically amplify the 5' terminal region of the NTRK3 gene, and a sense primer and an antisense primer that are designed so as to specifically amplify the 3' terminal region of the NTRK3 gene, can be used.

For example, a sense primer and an antisense primer that are designed so as to specifically amplify the 5' terminal region of the ETV6 gene, and a sense primer and an antisense primer that are designed so as to specifically amplify the 3' terminal region of the ETV6 gene, can be used.

Real-Time PCR Method

Further, in the PCR method, a more quantitative analysis can be carried out in the detection of the NTRK3 fusion or the ETV6 fusion gene, by using a PCR amplification monitor (real-time PCR) method in the gene amplification step (Genome Res., 6(10), 986, 1996). As the PCR amplification monitor method, for example, ABI PRISM7900 (PE Biosystems) can be used. The real-time PCR is a known method, and apparatuses and kits for the method are commercially available, and it can be easily carried out using them.

More particularly, for example, in the case where the NTRK3 fusion gene is the ETV6-NTRK3 fusion gene and is detected using mRNA as an index, the sense primer (5'-primer) is designed based on any portion derived from the ETV6 gene, and the antisense primer (3'-primer) is designed based on any portion derived from the NTRK3 gene.

In the case where the ETV6 fusion gene is the ETV6-NTRK3 fusion gene and is detected using mRNA as an index, the sense primer (5'-primer) is designed based on any portion derived from the ETV6 gene, and the antisense primer (3'-primer) is designed based on any portion derived from the NTRK3 gene.

Multiplex PCR

In the PCR method for detecting the NTRK3 fusion gene, a Multiplex PCR, in which all of the fusion polynucleotides are detected using a single reaction solution, can be designed by mixing the above-mentioned sense primers corresponding to each of the other genes that constitute the NTRK3 fusion gene together with the NTRK3 gene, and corresponding to multiple fusion points.

In the PCR method for detecting the ETV6 fusion gene, a Multiplex PCR, in which all of the fusion polynucleotides are detected using a single reaction solution, can be designed by mixing the above-mentioned sense primers corresponding to each of the other genes that constitute the ETV6 fusion gene together with the ETV6 gene, and corresponding to multiple fusion points.

Detection by Mass Spectrometry

A mass spectrometric method disclosed in JP2012-100628A can be used in order to analyze amplified fragments in the detection methods using the above-mentioned gene amplification reaction methods.

Primer Set Used in Detection

The primer set used in the detection method for detecting the NTRK3 fusion gene of the present invention is not particularly limited, so long as at least a portion of the NTRK3 fusion gene to be detected can be specifically amplified, and the NTRK3 fusion gene can be detected. Those skilled in the art can design the primer set, based on the nucleotide sequence of the polynucleotide to be detected.

The primer set used in the detection method for detecting the ETV6 fusion gene of the present invention is not particularly limited, so long as at least a portion of the ETV6 fusion gene to be detected can be specifically amplified, and the ETV6 fusion gene can be detected. Those skilled in the art can design the primer set, based on the nucleotide sequence of the polynucleotide to be detected.

Primers used in the PCR amplification monitoring method can be designed using a primer design software (for example, Primer Express; PE Biosystems), or the like. Since when the size of the PCR product is increased, the amplification efficiency becomes poor, it is preferable that the sense primer and the antisense primer are designed so that the size of the amplified product obtained when mRNA or cDNA is amplified as the target is 1 kb or less.

Detection by Hybridization Method mRNA can be detected by a hybridization method using a probe that hybridizes to a polynucleotide of at least a portion of the NTRK3 fusion gene to be detected.

As the detection using the hybridization technique, Northern hybridization, dot blotting, a DNA microarray method, and an RNA protection method can be exemplified.

Probe (for mRNA)

As the probe used in hybridization, a probe that hybridizes to a polynucleotide of at least a portion of the NTRK3 fusion gene or the ETV6 fusion gene, or a complementary strand thereof, under stringent conditions (preferably, under more stringent conditions), is preferable.

Detection of Fusion Protein

Any technique that is well-known by those skilled in the art and is used in the analysis of proteins, or any technique that is obtained by applying these techniques can be used, as the technique of detecting the NTRK3 fusion protein or the ETV6 fusion protein in samples obtained from a subject.

For example, as the method of detecting the NTRK3 fusion protein, an immunological measurement method (an immunoassay), an enzyme activity measurement method (an ELISA), a two-antibodies sandwich ELISA, a fluorescence immunoassay, a radioimmunoassay, a Western blotting, an immunohistochemical method, an immunoprecipitation method, an intercalated antibody-enhanced polymer (iAEP) method, and a FRET method, using an antibody that specifically recognizes the NTRK3 protein, an antibody that specifically recognizes a protein that is other than NTRK3 and constitutes the NTRK3 fusion protein together with the NTRK3 protein, or an antibody that specifically recognizes the NTRK3 fusion protein, can be exemplified. Further, mass spectrometry or amino acid sequencing can either be used in combination with these methods or alone.

For example, as the method of detecting the ETV6 fusion protein, an immunological measurement method (an immunoassay), an enzyme activity measurement method (an ELISA), a two-antibodies sandwich ELISA, a fluorescence immunoassay, a radioimmunoassay, a Western blotting, an immunohistochemical method, an immunoprecipitation method, an intercalated antibody-enhanced polymer (iAEP) method, and a FRET method, using an antibody that specifically recognizes the ETV6 protein, an antibody that specifically recognizes a protein that is other than ETV6 and constitutes the ETV6 fusion protein together with the ETV6 protein, or an antibody that specifically recognizes the ETV6 fusion protein, can be exemplified. Further, mass spectrometry or amino acid sequencing can either be used in combination with these methods or alone.

Hereinafter typical methods for detecting proteins will be exemplified, but the present invention is not limited to these methods.

Typical Techniques Used in Detection

The above-mentioned known methods, such as the following methods, may be used as detection methods using antibodies.

Immunohistochemical Method

For example, in the case where the NTRK3 fusion protein or the ETV6 fusion protein to be detected is the ETV6-NTRK3 fusion protein, a tissue section potential for the presence of the fusion protein to be detected can be subjected to immunostaining, using an anti-NTRK3 antibody that binds to a polypeptide at the C-terminal region of the NTRK3 protein, and an anti-ETV6 antibody that binds to a polypeptide at the N-terminal region of the ETV6 protein, to detect the presence of the fusion protein to be detected, by confirming that these antibodies are adjacent to each other.

Alternatively, the tissue section can be subjected to immunostaining, using an antibody that specifically binds to a polypeptide at the N-terminal region of the NTRK3 protein, and an antibody that specifically binds to a polypeptide at the C-terminal region of the NTRK3 protein, to detect the presence of the fusion protein to be detected, by confirming that these antibodies are located apart from each other.

Alternatively, the tissue section can be subjected to immunostaining, using an antibody that specifically binds to a polypeptide at the N-terminal region of the ETV6 protein, and an antibody that specifically binds to a polypeptide at the C-terminal region of the ETV6 protein, to detect the presence of the fusion protein to be detected, by confirming that these antibodies are located apart from each other.

Alternatively, the tissue section can be subjected to immunostaining, using an antibody that specifically binds to a polypeptide containing the fusion point, to detect the presence of the fusion protein to be detected.

Western Blotting

For example, in the case where the NTRK3 fusion protein or the ETV6 fusion protein to be detected is the ETV6-NTRK3 fusion protein, a cell extract potential for the presence of the fusion protein to be detected is subjected to electrophoresis, which is well-known for those skilled in the art, to separate the proteins contained in the cell extract from each other, and the separated proteins are blotted on a membrane.

Next, the membrane on which the proteins are blotted can be subjected to immunostaining, using an anti-NTRK3 antibody that binds to a polypeptide at the C-terminal region of the NTRK3 protein, and an anti-ETV6 antibody that binds to a polypeptide at the N-terminal region of the ETV6 protein, to detect the presence of the fusion protein to be detected, by confirming that the anti-NTRK3 antibody and the anti-ETV6 antibody are bound to the desired site on the membrane.

Alternatively, an antibody that specifically binds to a polypeptide containing the fusion point can be used to detect the presence of the fusion protein to be detected, by confirming that the antibody is bound to the desired site on the membrane.

Alternatively, an anti-NTRK3 antibody can be used to detect the presence of the fusion protein to be detected, by confirming that the antibody is bound to the ETV6-NTRK3 fusion protein on the membrane. In connection with this, the presence of the fusion protein to be detected can be detected by confirming that the anti-NTRK3 antibody is bound to a site different from the predicted site of the wild-type NTRK3 protein on the membrane.

Alternatively, an anti-ETV6 antibody can be used to detect the ETV6-NTRK3 fusion protein, on the same principle as that in the case of using the anti-NTRK3 antibody.

Immunoprecipitation

For example, in the case where the NTRK3 fusion protein or the ETV6 fusion protein to be detected is the ETV6-NTRK3 fusion protein, a cell extract potential for the presence of the fusion protein to be detected can be subjected to immunoprecipitation, using either an anti-NTRK3 antibody that binds to a polypeptide at the C-terminal region of the NTRK3 protein, or an anti-ETV6 antibody that binds to a polypeptide at the N-terminal region of the ETV6 protein, to detect the presence of the fusion protein to be detected, by detecting the precipitate using another antibody. After the immunoprecipitation and the detection as described above, it is preferable to further detect that the detected polypeptide has the same size as that of the polypeptide to be detected of interest, using a detection antibody.

Alternatively, a cell extract potential for the presence of the NTRK3 fusion protein to be detected can be subjected to immunoprecipitation, using an anti-NTRK3 antibody that binds to a polypeptide at the C-terminal region of the NTRK3 protein, and the precipitate can be subjected to mass spectrometry, to detect the presence of the fusion protein to be detected, by confirming the presence of a protein that has a mass different from that of the wild-type NTRK3 and binds to the NTRK3 antibody.

Alternatively, a cell extract potential for the presence of the ETV6 fusion protein to be detected can be subjected to immunoprecipitation, using an anti-ETV6 antibody that binds to a polypeptide at the N-terminal region of the ETV6 protein, and the precipitate can be subjected to mass spectrometry, to detect the presence of the fusion protein to be detected, by confirming the presence of a protein that has a mass different from that of the wild-type ETV6 and binds to the ETV6 antibody.

Antibody Used in Detection

The antibodies used in the detection method of the present invention are not particularly limited, so long as they specifically bind to the desired sites of the NTRK3 fusion protein or the ETV6 fusion protein. The antibodies may be monoclonal antibodies or polyclonal antibodies, and may be used in combination thereof. The antibodies may be immunoglobulins per se, or antibody fragments that retain the antigen binding activity, such as Fab, Fab', $F(ab')_2$, or Fv. In order to detect the binding of antibodies, any labeling or any signal amplification method, which is well-known for those skilled in the art, can be used.

Labeling Technique

In the detection method of the gene (genomic DNA, mRNA, cDNA, or the like) or the protein, the labeling of a probe, an amplified product, an antibody, or the like may be carried out using known techniques, for example, fluorescent labeling, radioactive labeling, enzyme labeling, or the like.

In the detection method using a probe, the probe can be labeled by a known method, as described above. For example, when a labeled nucleic acid probe is prepared from a BAC clone, a known technique, such as a nick translation method, a random prime method, or the like, can be used. In connection with this, the probe can be biotin-labeled using biotin-dUTP (for example, manufactured by Roche Applied Science), and can be further treated with a fluorescent substance, a radioisotope, an enzyme, or the like, to which avidin is bound, to label the probe.

In the detection method using antibodies, the antibodies can be labeled by a known method, as described above. The following labeling methods can be exemplified.

iAEP (Intercalated Antibody-Enhanced Polymer) Method

The sensitivity in staining can be improved by intercalating an intervening antibody between the first antibody that binds to the protein to be detected, and a polymer reagent (Takeuchi et al., Clin Cancer Res, 2009 May 1; 15(9): 3143-3149).

Fluorescence Resonance Energy Transfer (FRET)

For example, a probe utilizing a FRET phenomenon (FRET probe) can be used as a technique for detecting the proximity of the two antibodies. In the case where one antibody is labeled with a donor fluorescent substance (CFP or the like), and another antibody is labeled with an acceptor fluorescent substance (YFP or the like), when both are sufficiently adjacent to each other, YFP becomes the excited state, due to the FRET phenomenon, and emits fluorescence when returning to the ground state. The proximity of the two antibodies can be detected by detecting this fluorescence.

Judgment of Subject to Whom Treatment with NTRK3 Inhibitor is Applied

In the case where the NTRK3 fusion gene or the NTRK3 fusion protein to be detected by the detection method of the present invention is detected in a sample obtained from a subject, the subject is a subject (patient) with an NTRK3 fusion-positive cancer, and a subject to whom a treatment with an NTRK3 inhibitor is applied.

Judgment of Subject to Whom Treatment with ETV6 Inhibitor is Applied

In the case where the ETV6 fusion gene or the ETV6 fusion protein to be detected by the detection method of the present invention is detected in a sample obtained from a subject, the subject is a subject (patient) with an ETV6 fusion-positive cancer, and a subject to whom a treatment with an ETV6 inhibitor is applied.

Kit for Detection

The kit for detection of the present invention includes a kit for detection of the NTRK3 fusion gene to be detected, and a kit for detection of the NTRK3 fusion protein to be detected.

The kit for detection of the present invention includes a kit for detection of the ETV6 fusion gene to be detected, and a kit for detection of the ETV6 fusion protein to be detected.

The kit for detection of the NTRK3 fusion gene to be detected of the present invention, or the kit for detection of the ETV6 fusion gene comprises the probe that can be used in the FISH method, fusion assay or the FISH method, split assay in the detection method of the present invention; or the sense and antisense primers that are designed so as to specifically amplify at least a portion of the NTRK3 fusion gene or the ETV6 fusion gene to be detected in the detection method of the present invention. The sense and antisense primer set is a set of polynucleotides that are at least portions of the NTRK3 fusion gene or the ETV6 fusion gene, and that function as amplification primers for the polynucleotide to be amplified.

The kit for detection of the NTRK3 fusion protein to be detected of the present invention, or the kit for detection of the ETV6 fusion protein comprises the antibody that can be used in the detection method of the present invention.

Probe

The detection kit for the NTRK3 fusion gene of the present invention can comprise one probe, or a combination of two or more probes that can hybridize to a polynucleotide of at least a portion of the NTRK3 fusion gene, or a complementary strand thereof under stringent conditions, and that can detect the NTRK3 fusion gene.

The detection kit for the ETV6 fusion gene of the present invention can comprise one probe, or a combination of two or more probes that can hybridize to a polynucleotide of at least a portion of the ETV6 fusion gene, or a complementary strand thereof under stringent conditions, and that can detect the ETV6 fusion gene.

As the probe, one or more probes previously described in Techniques used in detection method can be exemplified.

For example, in the case where the NTRK3 fusion gene is the ETV6-NTRK3 fusion gene, the kit can comprise either of one or more (preferably two or more) probes that hybridize to a polynucleotide derived from the NTRK3 gene, or one or more (preferably two or more) probes that hybridize to a polynucleotide derived from the ETV6 gene; both of one or more probes that hybridize to a polynucleotide derived from the NTRK3 gene, and one or more probes that hybridize to a polynucleotide derived from the ETV6 gene; or one or more probes that hybridize to a polynucleotide containing the fusion point.

Primer Set

The kit for detection of the NTRK3 fusion gene of the present invention can comprise one set of primers that can specifically amplify at least a portion of the NTRK3 fusion gene, and that can detect the NTRK3 fusion gene; or a combination of two sets or more thereof.

The kit for detection of the ETV6 fusion gene of the present invention can comprise one set of primers that can specifically amplify at least a portion of the ETV6 fusion gene, and that can detect the ETV6 fusion gene; or a combination of two sets or more thereof.

As the primer set, one or more primer sets previously described in Embodiments of detection method of the present invention or Techniques used in detection method can be exemplified.

The primer set of the present invention preferably includes:

(1) a primer set for detecting the fusion gene of the ETV6 gene and the NTRK3 gene, comprising a sense primer designed from a polynucleotide encoding ETV6, and an antisense primer designed from a polynucleotide encoding NTRK3, wherein the antisense primer is composed of a nucleic acid molecule (preferably a nucleic acid molecule consisting of at least 16 nucleotides) that anneals to the "polynucleotide to be detected" under stringent conditions (preferably more stringent conditions), and the sense primer is composed of a nucleic acid molecule (preferably a nucleic acid molecule consisting of at least 16 nucleotides) that anneals to a complementary strand of the "polynucleotide to be detected" under stringent conditions (preferably more stringent conditions).

The primer set of the present invention includes the following primer set (2), as a more concrete embodiment of the above-mentioned primer set (1).

(2) A primer set comprising a sense primer (preferably SEQ ID NO: 4) consisting of at least 16 consecutive nucleotides in the region of nucleotides 1-1009 of SEQ ID NO: 1 (ETV6ex5-NTRK3ex15), and an antisense primer (preferably SEQ ID NO: 5) consisting of an oligonucleotide complementary to at least 16 consecutive nucleotides in the region of nucleotides 1010-1902 of SEQ ID NO: 1.

In these primer sets (1) and (2), it is preferable that the interval of the selected positions of the sense primer and the antisense primer is 1 kb or less, or that the size of the amplified product amplified by the sense primer and the antisense primer is 1 kb or less. The primer of the present invention generally has a strand length of 15-40 nucleotides, preferably 16-24 nucleotides, more preferably 18-24, and most preferably 20-24.

The primer set of the present invention can be used in the amplification and detection of the polynucleotide to be detected, in the detection method of the present invention. Each primer contained in the primer set of the present invention is not particularly limited, but can be prepared by chemical synthesis.

Antibody

The kit for detection of the NTRK3 fusion protein of the present invention comprises one antibody that specifically binds to any site of the NTRK3 fusion protein, or a combination of two or more thereof. More particularly, the antibodies described in detection of fusion protein can be exemplified.

The kit for detection of the ETV6 fusion protein of the present invention comprises one antibody that specifically binds to any site of the ETV6 fusion protein, or a combination of two or more thereof. More particularly, the antibodies described in detection of fusion protein can be exemplified.

For example, in the case where the NTRK3 fusion protein or the ETV6 fusion protein is the ETV6-NTRK3 fusion protein, the kit can comprise either of one or more (preferably two or more) antibodies that bind to a polypeptide derived from the NTRK3 protein, or one or more (preferably two or more) antibodies that bind to a polypeptide derived from the ETV6 protein; both of one or more antibodies that bind to a polypeptide derived from the NTRK3 protein, and one or more antibodies that bind to a polypeptide derived from the ETV6 protein; or one or more antibodies that bind to a polypeptide containing the fusion point of the NTRK3 fusion protein.

Screening Method of Inhibitor

Step of Screening Substance that Inhibits Polypeptide

According to the method of screening an inhibitor of the present invention, a substance that inhibits the polypeptide to be detected can be screened. The screening method comprises the steps of:

(1) bringing a test substance into contact with the polypeptide to be detected, or a cell expressing the polypeptide,
(2) analyzing whether or not the polypeptide is inhibited, and
(3) selecting a substance that inhibits the polypeptide.

The term "inhibition of the polypeptide" as used herein includes an inhibition of the activity of the polypeptide, and an inhibition of the expression of the polypeptide.

The term "inhibition" means at least a part of inhibition.

Step of Screening Inhibitor and its Index

The screening method of the present invention includes:
(A) a method in which a purified or crude polypeptide is used, and the inhibition of the activity of the polypeptide in vitro is regarded as an index;
(B) a method in which a cell expressing the polypeptide is used, and the inhibition of the activity of the polypeptide is regarded as an index; and
(C) a method in which a cell expressing the polypeptide is used, and the inhibition of the expression of the polypeptide is regarded as an index.

(A) A Method in which a Purified or Crude Polypeptide is Used, and the Inhibition of the Activity is Regarded as an Index The method (A) includes a method comprising the steps of: bringing a test substance into contact with the polypeptide in vitro; analyzing whether or not the activity of the polypeptide is inhibited by the test substance by comparing it with a control (a polypeptide with which the test substance is not brought into contact); and selecting the substance that inhibits the activity of the polypeptide.

The activity of the polypeptide in vitro can be measured using a known kinase activity assay. For example, the amount of ADP generated by the kinase reaction can be used as an index; a tyrosine phosphorylation level of the polypeptide can be used as an index; or a commercially available kinase activity assay kit can be used.

(B) A Method in which a Cell Expressing the Polypeptide is Used, and the Inhibition of the Activity is Regarded as an Index The method (B) includes a method comprising the steps of: bringing a test substance into contact with a cell expressing the polypeptide; analyzing whether or not the activity of the polypeptide is inhibited by the test substance by comparing it with a control (a cell with which the test substance is not brought into contact); and selecting the substance that inhibits the activity of the polypeptide.

The activity of the polypeptide in the cell can be measured using a known kinase activity assay. For example, the amount of ADP generated by the kinase reaction can be used as an index; a tyrosine phosphorylation level of the polypeptide can be used as an index; or a commercially available kinase activity assay kit can be used.

(C) A Method in which a Cell Expressing the Polypeptide is Used, and the Inhibition of the Expression is Regarded as an Index The method (C) includes a method comprising the steps of: bringing a test substance into contact with a cell expressing the polypeptide; analyzing whether or not the expression of the polypeptide is inhibited by the test substance by comparing it with a control (a cell with which the test substance is not brought into contact); and selecting the substance that inhibits the expression of the polypeptide.

The expression of the polypeptide in the cell can be analyzed by measuring the amount of the protein or mRNA. The amount of the protein can be measured by, for example, an ELISA method or immunoblotting. The amount of mRNA can be measured by, for example, an RT-PCR method or Northern blotting.

The NTRK3 fusion gene is a gene with oncogenic potential. Therefore, the polypeptide inhibitor, which is selected by the inhibitor screening method of the present invention, is useful as a therapeutic agent for the NTRK3 fusion-positive cancer, or a candidate thereof. The method of the present invention further comprises the step of confirming that the inhibitor has a therapeutic activity against the NTRK3 fusion-positive cancer, if desired.

The ETV6 fusion gene is a gene with oncogenic potential. Therefore, the polypeptide inhibitor, which is selected by the inhibitor screening method of the present invention, is useful as a therapeutic agent for the ETV6 fusion-positive cancer, or a candidate thereof. The method of the present invention further comprises the step of confirming that the inhibitor has a therapeutic activity against the ETV6 fusion-positive cancer, if desired.

The confirming step can be carried out using a known evaluation system, for example, an in vitro evaluation system using cultured cells, or a tumor-bearing animal model implanted with tumor cells.

The polypeptide-expressing cell can be obtained by introducing the polynucleotide of the present invention into a desired cell by a conventional method (see, for example, Molecular Cloning: A Laboratory Manual 4th Edition (2012), Cold Spring Harbor Laboratory Press). More particularly, for example, cDNA, which is the NTRK3 fusion gene or the ETV6 fusion gene of the present invention, is introduced into a recombinant vector, and the resulting DNA construct is introduced into cells to obtain the polypeptide-expressing cells (transformed cells).

Pharmaceutical Composition for Treating Cancer Containing Inhibitor

The pharmaceutical composition for treating an NTRK3 fusion-positive cancer (for example, digestive system cancer) of the present invention comprises the inhibitor against the NTRK3 fusion gene or its transcript. For example, the pharmaceutical composition contains, as the active ingredient, the inhibitor (for example, low molecular weight compounds, double-stranded nucleic acids (including siRNA), proteins (including an antibody or antibody fragment), peptides, or other compounds), which is obtained by the inhibitor screening method of the present invention, and further contains a pharmaceutically acceptable carrier, if desired.

The pharmaceutical composition for treating an ETV6 fusion-positive cancer (for example, digestive system cancer) of the present invention comprises the inhibitor against the ETV6 fusion gene or its transcript. For example, the pharmaceutical composition contains, as the active ingredient, the inhibitor (for example, low molecular weight compounds, double-stranded nucleic acids (including siRNA), proteins (including an antibody or antibody fragment), peptides, or other compounds), which is obtained by the inhibitor screening method of the present invention, and further contains a pharmaceutically acceptable carrier, if desired.

Inhibitor Against NTRK3 Fusion Gene or its Transcript, or ETV6 Fusion Gene or its Transcript Examples of the inhibitor against the NTRK3 fusion gene or its transcript include a kinase inhibitor (for example, an inhibitor for NTRK3), and an inhibitor against another gene that constitutes the fusion gene together with the NTRK3 gene, or its transcript.

Examples of the inhibitor against the ETV6 fusion gene or its transcript include a kinase inhibitor (for example, an inhibitor for ETV6), and an inhibitor against another gene that constitutes the fusion gene together with the ETV6 gene, or its transcript.

Low Molecular Weight Compounds Among inhibitors, examples of the low molecular weight compound include AG879 (CAS148741-30-4), and compounds disclosed in WO2008/045627 or WO2008/073480.

Examples of the inhibitor against the ETV6-NTRK3 fusion gene or its transcript include PKC412 (also called midostaurin; Chi H T, Ly B T, Kano Y, Tojo A, Watanabe T, Sato Y. ETV6-NTRK3 as a therapeutic target of small molecule inhibitor PKC412. Biochem Biophys Res Commun. 2012 Dec. 7; 429 (1-2): 87-92.)

Double-Stranded Nucleic Acids

The double-stranded nucleic acid is composed of a double-stranded nucleic acid (RNA or DNA) portion, and preferably overhangs at the 3' terminus of the sense strand and the antisense strand, and induces RNAi. RNAi is an evolutionally conserved phenomenon, and occurs through the double-stranded nucleic acid consisting of 21-23 nucleotides, which is generated by RNase III endonuclease (Genes Dev. 15, 485-490, 2001). The overhangs at the 3' terminus are nucleic acids consisting of one or two arbitrary nucleotides, and two nucleotides are preferable. In connection with this, the number of nucleotides (21-23 nucleotides) means the number of nucleotides that constitute the sense strand or the antisense strand including each overhang. The nucleotide numbers in the sense strand and the antisense strand may be the same or different, and are preferably the same.

The ribonucleic acids, which constitute the overhangs at the 3'-terminus of the double-stranded nucleic acid, may be, for example, U (uridine), A (adenosine), G (guanosine), or C (cytidine). The deoxyribonucleic acids, which constitute the overhangs at the 3'-terminus, may be, for example, dT (deoxythymidine), dA (deoxyadenosine), dG (deoxyguanosine), or dC (deoxycytidine).

The double-stranded nucleic acid, which may be used as the active ingredient of the pharmaceutical composition of the present invention, is not particularly limited, so long as it has the inhibitory activity against the NTRK3 fusion gene, or the inhibitory activity against the ETV6 fusion gene. For example, it can be designed on the basis of the nucleotide sequence of a polynucleotide, in which the double-stranded portion contains a fusion point, such as a nucleotide sequence containing nucleotides 1009-1010 of SEQ ID NO: 1. Alternatively, it can be designed on the basis of the nucleotide sequence of a polynucleotide, in which the double-stranded portion encodes the kinase portion. The double-stranded nucleic acid of the present invention can be prepared by a conventional method (for example, J. Am. Chem. Soc., 120, 11820-11821, 1998; and Methods, 23, 206-217, 2001). Companies which manufacture double-stranded nucleic acids under contract (for example, RNAi Inc.) are well-known to those skilled in the art, and can be used in the preparation of double-stranded nucleic acid. Double-stranded nucleic acid can be designed by an siRNA sequence design system (siDirect (trademark), RNAi Inc.)

Proteins and Antibodies

The antibody, which may be used as the active ingredient of the pharmaceutical composition of the present invention, is not particularly limited, so long as it can inhibit the transcript of the NTRK3 fusion gene or the transcript of the ETV6 fusion gene, preferably the transcript of the ETV6-NTRK3 gene. For example, an antibody that inhibits the activity (preferably kinase activity) of the NTRK3 fusion protein or the ETV6 fusion protein can be exemplified.

EXAMPLES

The present invention will now be further illustrated by, but is by no means limited to, the following Examples.

Example 1 Detection of ETV6 Genetic Abnormalities by FISH Method in Clinical Specimens A method of observing the translocation of a gene of interest by staining the 5' terminal region and the 3' terminal region of the gene with different dyes is known. This method, which is a kind of FISH method, is called a split assay. In the split assay, each of the 5' terminal region and the 3' terminal region of the target gene, of which the chromosomal translocation is to be examined, is stained using probes labeled with different fluorescent dyes. For example, when fluorescent-labeling is carried out using two types of probes respectively labeled with TexasRed (red) and FITC (green), two yellow signals (a state in which the green and red signals are adjacent to each other) are detected in the normal case, and the green signal and the red signal are detected apart from each other in the case of the translocation or inversion.

ETV6 genetic abnormalities were detected by a FISH method, split assay in clinical specimens. Surgically-removed, and 20% formalin-fixed, paraffin-embedded colorectal cancer tissues were sliced at a thickness of 4 am, and placed on slides to prepare pathological sections. The FISH method was carried out in accordance with the method described in a reference (Takeuchi K, Choi Y L, Soda M, Inamura K, Togashi Y, Hatano S, Enomoto M, Takada S, Yamashita Y, Satoh Y, Okumura S, Nakagawa K, Ishikawa Y, Mano H. Multiplex reverse transcription-PCR screening for EML4-ALK fusion transcripts. Clin Cancer Res. 2008; 14: 6618-6624.). The prepared, unstained sections were treated using a Histology FISH accessory kit (Dako), and then were hybridized with a BAC (bacterial artificial chromosome) clone (clone No. RP11-63901, RP11-107715), which covered the 5' terminal region of the ETV6 gene and was fluorescent-labeled with green (FITC), and a BAC clone (clone No. RP11-297N18), which covered the 3' terminal region of the ETV6 gene and was fluorescent-labeled with red (TexasRed). The sections were further stained with 4,6-diamino-2-phenylindole. A fluorescence microscope BX51 (Olympus Corporation) was used for fluorescence observation. As a result, a section, in which the green signal and the red signal were observed apart from each other, and in which genomic structure abnormalities were suggested, was found. From the examination of about 1500 cases of pathological specimens, 1 specimen case (derived from a patient with colon cancer) that suggested the genomic structure abnormalities in the ETV6 gene region was found.

Example 2 Identification of ETV6 Fusion Polynucleotide in Clinical Specimen

RNA from the tissue, in which the ETV6 genomic structure abnormalities were suggested by the FISH method analysis, was used as a template, in accordance with the protocol of a commercially available RACE kit (SMARTer (registered trademark) RACE cDNA Amplification Kit; Clonetech), to analyze a gene that was present at the 3' end of the 5' terminal region of the ETV6 gene. More particularly, the first strand cDNA was synthesized using 0.5 µg of RNA obtained from the clinical specimen. With respect to a 3'-RACE (rapid amplification of cDNA ends) PCR, a universal primer (UPM) contained in the kit, and a forward primer (SEQ ID NO: 3) were used to carry out the PCR reaction using a DNA polymerase (AmpliTaq Gold (registered trademark); Life Technologies Japan Ltd.).

The resulting RACE product was electrophoresed, and a DNA fragment of around 1-2 kip was purified. After TA cloning was carried out in accordance with a conventional method, its sequence was analyzed. As a result, it was clarified that part of a kinase region of an NTRK3 gene was fused to the 3' end of the ETV6 gene. It was revealed that the fusion was generated between exon 5 of the ETV6 gene and exon 15 of the NTRK3 gene.

The presence of the fusion gene of these genes and its transcriptional product in a digestive system cancer had not been reported, and it was shown for the first time (Knezevich S R et al., Nat Genet. 1998 February; 18(2): 184-187. Tognon C, et al., Cancer Cell. 2002 November; 2(5): 367-76). Further, the presence of the NTRK3 in a digestive system cancer had not been reported, and it was shown for the first time (Hisaoka M et al., J Pathol. 2002 August; 197(5): 661-67).

With respect to the fusion gene, transformation in transduced cells, and oncogenic potential in transduced-cell-transplanted mice were shown, and it is suggested that the presence of the fusion gene or its transcriptional product is a cause of cancer in the expression site (Wai D H et al., Oncogene. 2000 Feb. 17; 19(7): 906-15).

TABLE 1

| Primer | Sequence (5'→3') | SEQ ID NO: |
|---|---|---|
| ETV6-874F | GAAGCCCATCAACCTCTCTCATCGG | 3 |
| ETV6-428F | AGCCGGAGGTCATACTGCAT | 4 |
| NTRK3-1632R | CAGTTCTGCTTCAGCACG | 5 |

Example 3 Detection of ETV6-NTRK3 Fusion Gene

The primers as shown in Table 1 were used to detect the fusion gene by an RT-PCR, by which the region containing the fusion point was directly amplified, and it was shown that the cDNA of the fusion gene was present in the cancer tissue. More particularly, a PCR was carried out using an RNA template derived from the specimen, and a forward primer ETV6-428F (SEQ ID NO: 4) designed on the ETV6 gene and a reverse primer NTRK3-1632R (SEQ ID NO: 5) designed on the NTRK3 gene. The amplified product was electrophoresed, and a band having the size (1037 bp) expected from the primer setting position was observed. It was shown that the fusion gene could be detected, using a clinical specimen, by designing primers on these genes.

Example 4 Detection of ETV6-NTRK3 Fusion Gene by FISH Method, Fusion Assay in Clinical Specimens In order to confirm that the fusion gene was fused on the genome, each of the BAC clones shown in Table 2 was appropriately combined with one another, and detection was carried out by a FISH method, fusion assay.

TABLE 2

| Gene | BAC clone | |
|---|---|---|
| | FITC | TexasRed |
| NTRK3 | CTD-3188J15<br>CTD-2573H21<br>RP11-285I14 | RP11-624F1<br>RP11-948I15 |
| ETV6 | RP11-639O1<br>RP11-1077I5 | RP11-297N18 |

In the FISH method, fusion assay, two target gene regions, which are adjacent to each other by chromosomal translocation, are stained by probes labeled with different fluorescent dyes. For example, when fluorescent-labeling is carried out using two types of probes respectively labeled with TexasRed (red) and FITC (green), the green signal and the red signal are detected as each signal (a state in which the green signal and the red signal are present apart from each other) in the normal case, and the green signal and the red signal overlap with each other and are detected as a yellow signal in the case where the two gene regions are adjacent to each other by translocation or inversion. More particularly, a combination of a BAC clone (clone No. RP11-639O1, RP11-1077I5), which covered the 5' terminal region of the ETV6 gene and was fluorescent-labeled with green (FITC), and a BAC clone (clone No. RP11-624F1, RP11-948I15), which covered the 3' terminal region of the NTRK3 gene and was fluorescent-labeled with red (TexasRed), was used. A fluorescence microscopy BX51 (Olympus Corporation) was used for fluorescence observation. As a result of the fusion assay on the pathological section, on which the fusion gene was positive in Example 3, a signal (yellow), showing that the 5' terminal region of the ETV6 gene was adjacent to the 3' terminal region of the NTRK3 region, was observed, and it was confirmed that the fusion gene was generated by chromosomal translocation.

It was found that this method could be used as a method of detecting the presence of the fusion gene.

Example 5 Detection of ETV6 Gene or NTRK3 Gene by FISH Method, Split Assay in Clinical Specimens The FISH method, split assay of the ETV6 gene or the NTRK3 gene was carried out in accordance with the method described in Example 1. Pathological sections were prepared in a similar manner to that of Example 1. The prepared, unstained sections were treated using a Histology FISH accessory kit (Dako).

In the case of the split assay for ETV6, the sections were hybridized with a BAC clone (clone No. RP11-639O1, RP11-1077I5), which covered the 5' terminal region of the ETV6 gene and was fluorescent-labeled with green (FITC), and a BAC clone (clone No. RP11-297N18), which covered the 3' terminal region of the ETV6 gene and was fluorescent-labeled with red (TexasRed). The sections were further stained with 4,6-diamino-2-phenylindole.

In the case of the split assay for NTRK3, the sections were hybridized with a BAC clone (clone No. CTD-3188J15, CTD-2573H21, RP11-285I14), which covered the 5' terminal region of the NTRK3 gene and was fluorescent-labeled with green (FITC), and a BAC clone (clone No. RP11-624F1, RP11-948I15), which covered the 3' terminal region of the NTRK3 gene and was fluorescent-labeled with red (TexasRed). The sections were further stained with 4,6-diamino-2-phenylindole. A fluorescence microscopy BX51 (Olympus Corporation) was used for fluorescence observation. On the pathological section, on which the fusion gene was positive in Example 3, a section, in which the green signal and the red signal were observed apart from each other, and in which genomic structure abnormalities were suggested, was found.

It was found that this method could be used as a method of detecting the presence of the fusion gene.

As described above, it was revealed in the present invention that the fusion gene of the NTRK3 gene was present in some of patients with a digestive system cancer, and the fusion gene was a cause of cancer. Namely, it was clarified that cancer patients to be treated with an NTRK3 inhibitor could be selected by detecting the NTRK3 fusion gene, preferably ETV6ex5-NTRK3ex15.

INDUSTRIAL APPLICABILITY

The detection method of the present invention is useful in the judgment of NTRK3 fusion-positive cancer patients. The detection kit and the primer set of the present invention can be used in the detection method. The inhibitor screening method of the present invention can be used in the screening of drugs effective for the treatment of the NTRK3 fusion-positive cancer patients. The drugs obtained by the screening can be used as the active ingredient for a pharmaceutical composition for the treatment of the NTRK3 fusion-positive cancer. It is possible to treat the cancer by administering the drug to a patient, who has been judged to be the NTRK3 fusion-positive cancer patient by the detection method.

The detection method of the present invention is useful in the judgment of ETV6 fusion-positive cancer patients. The detection kit and the primer set of the present invention can be used in the detection method. The inhibitor screening method of the present invention can be used in the screening of drugs effective for the treatment of the ETV6 fusion-positive cancer patients. The drugs obtained by the screening can be used as the active ingredient for a pharmaceutical composition for the treatment of the ETV6 fusion-positive cancer. It is possible to treat the cancer by administering the drug to a patient, who has been judged to be the ETV6 fusion-positive cancer patient by the detection method.

Although the present invention has been described with reference to specific embodiments, various changes and modifications obvious to those skilled in the art are possible without departing from the scope of the appended claims.

Free Text in Sequence Listing

The nucleotide sequences of SEQ ID NOS: 3 to 5 in the sequence listing are synthetic primer sequences.

The invention claimed is:

1. A method for detecting an Ets Variant6 (ETV6)-Neutrophic Tyrosine Kinase, Receptor, Type3 (NTRK3) fusion gene, comprising the steps of:
   preparing a colorectal cancer tissue obtained from a subject, and
   detecting the cleavage of a gene encoding an ETV6 protein or an NTRK3 protein, or the presence of a fusion gene encoding a fusion protein constructed from the ETV6 protein and the NTRK3 protein.

2. The method of claim 1, wherein the ETV6-NTRK3 fusion gene is a polynucleotide encoding the polypeptide selected from the group consisting of the following (a) and (b):
   (a) a polypeptide consisting of the amino acid sequence of SEQ ID NO: 2, and
   (b) a polypeptide with oncogenic potential comprising the amino acid sequence of SEQ ID NO: 2.

3. The method of claim 1, wherein the fusion gene is DNA or mRNA.

* * * * *